United States Patent [19]
Haley et al.

[11] Patent Number: 5,800,991
[45] Date of Patent: Sep. 1, 1998

[54] NUCLEOTIDE OR NUCLEOSIDE PHOTOAFFINITY COMPOUND MODIFIED ANTIBODIES, METHODS FOR THEIR MANUFACTURE AND USE THEREOF AS DIAGNOSTICS AND THERAPEUTICS

[75] Inventors: Boyd E. Haley, Nicholasville; Heinz Kohler, Lexington; Krishnan Rajagopalan, Lexington; Gabriela Pavlinkova, Lexington, all of Ky.

[73] Assignee: University of Kentucky Research Foundation, Lexington, Ky.

[21] Appl. No.: 681,432

[22] Filed: Jul. 23, 1996

Related U.S. Application Data

[63] Continuation-in-part of Ser. No. 208,822, Mar. 11, 1994, Pat. No. 5,596,081.

[51] Int. Cl.$^6$ .................... G01N 33/53; C07K 16/00; C12P 21/00; C12Q 1/68
[52] U.S. Cl. .................... 435/6; 435/7.9; 435/7.5; 530/391.1; 530/391.3; 530/391.5; 530/391.7; 530/391.9
[58] Field of Search ................ 435/7.9, 7.92, 435/6, 7.5; 530/391.1, 391.3, 391.5, 391.7, 391.9

[56] References Cited

U.S. PATENT DOCUMENTS

| | | |
|---|---|---|
| 4,861,579 | 8/1989 | Meyer et al. |
| 5,045,451 | 9/1991 | Uhr et al. ............... 435/7.23 |
| 5,106,951 | 4/1992 | Morgan et al. ............ 530/391.9 |
| 5,272,055 | 12/1993 | Haley ........................... 435/6 |

OTHER PUBLICATIONS

Canevari, et al., *Annals of Oncology*, vol. 5, pp. 698–701, 1994.
Stein, et al., *Science*, vol. 261, pp. 1004–1012, 1993.
Borrebaeck, *J. Immunol. Methods*, vol. 123, pp. 157–165, 1989.
Spalding, *Bio/Technology*, vol. 11, pp. 428–429, 1993.
Osband, et al., *Immunology Today*, vol. 11, No. 6, pp. 193–195, 1990.
Harris et al., *Tibtech*, vol. 11, pp. 42–44, 1993.
Bach et al., Immunology Today, vol. 14, No. 9, pp. 421–425, 1993.
Waldmann, Science, vol. 252, pp. 1657–1662, 1991.

*Primary Examiner*—Toni R. Scheiner
*Attorney, Agent, or Firm*—Burns, Doane, Swecker & Mathis, L.L.P.

[57] ABSTRACT

Sites on antibodies having affinity for photoaffinity compounds, in particular purine or azidopurine containing compounds are taught. Such photoaffinity sites are contained on a conserved region of different antibody molecules. These sites provide for the site-specific attachment of nucleotide photoaffinity compounds to antibodies, e.g., ATP- or GTP-analog photoaffinity compounds by photochemical means. These nucleotide photoaffinity compounds may additionally be attached to molecules having a desired therapeutic or diagnostic activity, and the resultant conjugates used as diagnostics or therapeutics.

15 Claims, 21 Drawing Sheets

T1

S1C5 VK: QIVLTQSPAI NSASLGERVT MTCTASSSVS SSYFHWYQQK QGSSPKLWIY
B019 VK: DIVLTQSPAS LSASVGETVT ITCRASENIY SYLLWYQQK QGKSPQLLVY

S1C5 VK: TTSNLASGVP ARFSGSGSGT SYSLTISSME AEDAATYYCH QYHRSPLTFG AGTKLELKRA
B019 VK: NAKTLAEGVP SRFSGSGSGT QFSLKINSLQ PEDFGSYFCQ HHFGTPWTFG GGTSLEIKRA

S1C5 VH: QVQLQQSDAI LVKPGASVKI SCKASGYTFT DHVTHWVKQR PEQLGEWIGF ISPGNGDIRY
B019 VH: EVNLEESGGG LVQPGGSMKL SCAASGFTES DAWMDWVRQS PEKGLEWVAE IRTKVNNHAT

S1C5 VH: NEKF KDK ATADKSSSTA YMQLNSLTSE DSAVYFCKRS FYYYDDNYGD YWGQGTTLTV SAAK
B019 VH: YYAESVKGRF TISRDDSKSN VYLQMNSLRV EDTGIYYCTM AYYE A YWGQGTLVTV SAAK

NUCLEOTIDE OR NUCLEOSIDE PHOTOAFFINITY COMPOUND MODIFIED ANTIBODIES, METHODS FOR THEIR MANUFACTURE AND USE THEREOF AS DIAGNOSTICS AND THERAPEUTICS

CROSS REFERENCE TO RELATED APPLICATIONS

This application is a continuation-in-part of U.S. Ser. No. 08/208,822, filed March 11, 1994, now U.S. Pat. No. 5,596,081.

FIELD OF THE INVENTION

The present invention relates to the discovery of a novel site or sites on antibodies having high affinity for nucleotide or nucleoside photoaffinity compounds. The present invention further relates to the use of said novel site or sites as a target for photoaffinity labeling using nucleotide or nucleoside photoaffinity compounds and for the attachment of molecules having a particular chemical or biological activity. In particular, the present invention concerns a site or sites on antibodies having high affinity for purine or purine derivative containing photoaffinity compounds, e.g., ATP- or GTP-analog photoaffinity compounds and the use of these sites as targets for purine or purine derivative photoaffinity compounds or other heterocyclic base containing compounds which have affinity for these sites and for the attachment of molecules having a particular chemical or biological activity.

The present invention further relates to identification of a novel photoaffinity site comprised on antibody materials by computer modeling and other methods in order to identify its specific position on antibody molecules. The identification of this specific site, and specifically the specific amino acid residues, will allow this site to be protected prior to photoaffinity attachment of desired compounds and also enable similar sites to be identified on other proteins.

The present invention further relates to compositions, methods, and test kits which contain or use the subject nucleotide photoaffinity labeled antibodies. The present invention still further relates to novel compositions, methods and test kits which use the procedure of photoaffinity labeling with nucleotide affinity probes, to attach molecules having a desired chemical or biological activity to antibody molecules.

BACKGROUND OF THE INVENTION

Antibodies are specific immunoglobulin molecules produced by vertebrate immune systems in response to challenge by foreign proteins, glycoproteins, cells, or other typically foreign substances. The sequence of events which permits an organism to overcome invasion by foreign cells or to rid the system of foreign substances is at least partially understood. An important part of this process is the manufacture of antibodies which bind specifically to a particular foreign antigenic substance. The binding specificity of such polypeptides to a particular antigen is highly refined, and the multitude of specificities capable of being generated by an individual vertebrate is remarkable in its complexity and variability. Thousands of antigens are capable of eliciting antibody responses, each almost exclusively directed to the particular antigen which elicited it.

The immunoglobulin molecule consists of two variable domains and several constant domains mediating biological effector mechanisms (Nisonoff et al, *The Antibody Molecule* (eds. Dixon, F. J. & Kunkel, H. G.), Academic Press (1975)). The variable domains contain hypervariable regions which are involved in the formation of the antigen-binding site. Biochemical and structural studies have shown that antigen binding is mediated by the assemblage of six so-called complementary determining regions, CDR[1]. Framework regions, FR, interspersed between CDRs, are believed to maintain the overall fold of the variable Ig domains; however, crystallographic studies have shown that framework regions also are involved in antigen contact and thus participate in the generation of antibody specificity (Fields et al, *Nature*, 374:739–742). For years antigen binding has been considered the only function associated with the variable domains of antibodies.

Immunoglobulins include both antibodies, as above described, and analogous protein substances which lack antigen specificity. The latter are produced at low levels by the lymph system and in increased levels by myelomas.

Antibodies are produced by B lymphocytes and represent the humoral arm of the immune defense system. Because of their antigen specificity, antibodies comprise numerous diagnostic and therapeutic applications. For example, they can be used as specific immunoprecipitating agents to detect the presence of an antigen which they specifically bind by coupling the antigen-antibody reaction with suitable detection techniques such as labeling with radioisotopes or with detectable enzymes (RIA, EMIT, and ELISA). Antibodies are thus the foundation of immunodiagnostic tests for many antigenic substances.

Another important application of antibodies involves their use as therapeutics. The therapeutic administration of antibodies has recently been described for the treatment of numerous disease conditions including cancer, and numerous infectious diseases.

The therapeutic usage of antibodies has been the focus of greater interest since the development of monoclonal antibody/hybridoma technology by Kohler and Milstein (*Proc. Natl. Acad. Sci., USA*, 77:2197 (1980)). Monoclonal antibodies, which are produced by hybridomas, are preferable to polyclonal antibodies because of their greater antigenic specificity. Monoclonal antibodies have a lesser tendency than polyclonal antibodies to non-specifically bind to non-targeted moieties, e.g., cells which do not express the corresponding antigen. However, monoclonal antibodies still suffer from some disadvantages, e.g., they tend to be contaminated with other proteins and cellular materials of hybridoma (mammalian) origin. Also, hybridoma cell lines tend to be unstable and may alter the production of the antibody produced or stop secreting the antibody altogether.

In an effort to obviate some of the problems associated with polyclonal and monoclonal antibodies, and further to obtain a reproducible supply of antibodies having a defined binding specificity, researchers have used recombinant techniques to produce immunoglobulins which are analogous or modified in comparison to antibodies normally found in vertebrate systems. For example, U.S. Pat. No. 4,816,397, issued on Mar. 28, 1989, to Boss et al and U.S. Pat. No. 4,816,567, issued on Mar. 28, 1989, to Cabilly et al disclose recombinant immunoglobulins and immunoglobulin fragments, and methods for their production.

To enhance or modify the properties of recombinant antibodies, it is further known to produce mutant or chimeric antibodies, e.g., which comprise sequences from several different mammalian species or bispecific antibodies which comprise antigenic binding sequences from two different antibodies. For example, humanized antibodies which comprise antigen-binding sites from a non-human species (typically murine) but wherein the remainder of the immunoglobulin is of human origin are known in the art, and have been reported to have significant potential as therapeutics because of their reduced antigenicity. It is further known to produce recombinant antibodies of single chain form, which completely lack constant domain sequences but which bind antigen. (See. Bird et al. *Science*, 242, 423–426 (1988)).

In order to increase the efficacy of antibody molecules as diagnostic or therapeutic agents, it is conventional to covalently bind or complex desired molecules thereto, in particular effector or reporter molecules. Effector molecules essentially comprise molecules having a desired activity, e.g., cytotoxic activity. By contrast, a reporter molecule is defined as any moiety which may be detected using an assay. Examples of effector molecules which have been attached to antibodies include by way of example, toxins, anti-tumor agents, therapeutic enzymes, radionuclides, antiviral agents, chelating agents, cytokines, growth factors, and polynucleotides. Examples of reporter molecules which have been conjugated to antibodies include, by way of example, enzymes, radiolabels, haptenes, ligands, such as biotin, fluorescent labels, phosphorescent molecules, chemiluminescent molecules, chromophores, luminescent molecules, and colored particles.

While it is desirable to attach molecules to antibodies in order to impart a desired activity to the antibody or provide for the detection thereof, the attachment of desired molecules to antibodies is not always possible to carry out conveniently, or effectively, because such attachment may result in loss of antibody activity. In particular, current methods for generating radiolabeled antibodies for diagnostic and therapeutic use suffer from such limitations. For example, the ratio of target-specific versus non-specific uptake of radiolabeled antibodies used in tumor imaging is often low, resulting in unclear images or missing tumor sites. Moreover, the low therapeutic index of radiolabeled antibodies limits the use of high radiation doses in radiation therapy.

The underlying reason for such problems is largely because the labeling chemistry for introduction of the radiolabel results in the partial denaturation of the antibody structure, which in turn causes the antibodies to aggregate in vivo or in vitro. Aggregated and damaged immunoglobulins are recognized by scavenger cells in the body, such as macrophages and Kupffer cells in the liver and lung.

Another problem is that most coupling strategies result in non site-specific attachment of the molecule to the antibody molecule, in particular, attachment may occur at antibody residues which are essential for antigen binding or other antibody functions. For instance, a known site of attachment of desired molecules to antibody molecules comprise thiol groups, since thiol groups occur naturally in proteins as cysteine residues. However, such residues are relatively uncommon, are often inside the molecule and are frequently involved in forming disulfide bridges within or between protein molecules. Thus, there is a danger that if a naturally occurring cysteine residue is used as a site of attachment, it will interfere with the normal folding and stabilization of the antibody protein.

In an effort to obviate such problems, alternative strategies have been developed which provide for site-selective attachment of a desired molecules to antibodies, without loss of antigen-binding activity. For example, it is known to produce recombinant antibodies comprising cysteine residues introduced into their surface structure to provide a thiol group which is available for covalent binding to an effector or reporter molecule. This method has been reported to facilitate the site-specific attachment of desired molecules without loss of antigen binding properties. (See. U.S. Pat. No. 5,219,996, issued on Jun. 15, 1993, to Bodmer et al.) However, this is not always possible or convenient since it obviously requires the possession of a recombinant DNA encoding the particular antibody.

It has further been proposed to derivatize immunoglobulins by selectively introducing sulfhydryl groups in the Fc region of an immunoglobulin, using reaction conditions which purportedly do not result in alteration of the antibody combining site. Antibody conjugates produced according to this methodology are disclosed to exhibit improved longevity, specificity and sensitivity (U.S. Pat. No. 5,196,066, issued on Mar. 2, 1993, to Bieniarz et al).

Site-specific attachment of effector or reporter molecules, wherein the reporter or effector molecule is conjugated to a carbohydrate residue in the Fc region has also been disclosed in the literature. (See. e.g., O'Shannessy et al. *J. Immun. Meth.*, 99, 153–161 (1987)). This approach has been reported to produce diagnostically and therapeutically promising antibodies which are currently in clinical evaluation.

Another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this is disadvantageous since it results in loss of antigen binding by the antibody conjugate.

Recently additional sites for binding, biological active molecules have been discovered in the Ig molecule. Besides the canonical antigen binding site, these so-called unconventional sites (Sasso et al. *J. Immunol.*, 142:2778–2783 (1989); Shorki et al. *J. Immunol.*, 146:936–940 (1991); Silvermann et al. *J. Clin. Invest.*, 96:417–426 (1995); Cleary et al. *Trends Microbiol.*, 4:131–136 (1994); Lenert et al. *Science*, 248:1639–1643 (1990); Berberian et al. *Science*, 261:1588–1591 (1993); Kreier et al. *Infection, Resistance and Immunity*, Harper & Row, New York, (1991)) reside also in the variable domain and can bind pathogens. B-cell superantigens, the T cell co-receptor CD4 and the HIV-1 envelope. In addition, the variable domain is involved in Ig self-binding (Kang et al. *Science*, 240:1034–1036 (1988)), and contains epitopes (idiotopes) recognized by anti-antibodies (Kohler et al. *Methods Enzymol.*, 178:3 (1989)). Similar to the joint involvement of CDR and FR regions in antigen binding, the unconventional binding sites also draw on CDR and FR regions. Docking to these unconventional sites does not typically interfere with antigen binding, suggesting that these sites may be a part of the biological functions of immunoglobulins.

Thus, based on the foregoing, it is clear that there still exists a significant need in the art for improved methods of attaching molecules to antibodies, in particular effector or reporter molecules, which are site-specific and which moreover result in antibody conjugates having substantially unaltered structure and biological activity, most especially antigen binding activity.

Molecules containing azido groups have been shown to form covalent bonds to proteins through reactive nitrene intermediates, generated by low intensity ultraviolet light. Potter & Haley. *Meth. in Enzymol.*, 91, 613–633 (1983). In particular, 2- and 8-azido analogues of purine nucleotides have been used as site directed photoprobes to identify nucleotide binding proteins in crude cell extracts. Owens &

Haley, *J. Biol. Chem.*, 259:14843–14848 (1987); Atherton et al, *Biol. of Reproduction*, 32, 155–171 (1985). The 2- and 8-azido nucleotides have also been used to map nucleotide binding domains of purified proteins. Khatoon et al, *Ann. of Neurology*, 26, 210–219 (1989); King et al, *J. Biol. Chem.*, 269, 10210–10218 (1989); and Dholakia et al, *J. Biol. Chem.*, 264, 20638–20642 (1989).

Photoaffinity probes have been used to determine specific nucleotide binding sites on a biologically active recombinant peptide molecule. Campbell et al, *PNAS*, 87, 1243–1246 (1990). The probes have also been used to study enzyme kinetics of purified proteins. Kim et al, *J. Biol. Chem.*, 265, 3636–3641 (1990).

Recently, ATP or GTP analog photoaffinity labeled probes have been used to detect a glutamine synthetase nucleotide binding protein having an apparent molecular weight of about 42,000 proteins to aid in the diagnosis of Alzheimer's disease in a mammal. U.S. Ser. No. 08/138,109, filed on Oct. 20, 1993, by Haley et al. Additionally, ATP or GTP analog photoaffinity-labeling reagents have been disclosed for use in the detection of particular nucleotide binding proteins to aid in the diagnosis of cancer in a mammal and in the diagnosis of leukemia in a mammal. (Id.)

However, while it had been previously known to use nucleotide photoaffinity probes, and specifically purine containing photoaffinity analogs (GTP- and ATP-analogs), to map nucleotide binding domains of purified proteins and to identify specific nucleotide binding sites on recombinant peptide molecules, the use of nucleotide photoaffinity probes to label antibodies has not been previously reported in the literature. This is essentially because it had not been previously known that antibody molecules comprise nucleotide photoaffinity sites, and in particular, sites having high affinity for purine, azidopurine and other similar heterocyclic bases, which may be efficiently photolabeled using appropriate photoaffinity probes.

OBJECTS AND SUMMARY OF THE INVENTION

It is, therefore, an object of this invention to identify nucleotide or nucleoside affinity sites on antibodies which provide for the site specific photoinsertion of desired molecules to antibodies. It is further a specific object of the invention to characterize the effects of these affinity sites on antibody function.

It is a more specific object of this invention to identify a site or sites on antibodies having high affinity for purines, azido-purines and other similar heterocyclic organic compounds, in particular ATP- or GTP-analog photoaffinity compounds.

It is another object of the invention to identify the specific amino acid residues which constitute a 3-dimensional photoaffinity binding site on antibody molecules (by computer modeling and other methods) which binding site provides for the photoaffinity attachment of purines, azido-purines and other similar heterocyclic organic compounds, in particular ATP- or ATP-analog photoaffinity compounds.

It is another specific object of the invention to provide methods for coupling desired molecules, e.g., effector or reporter molecules to an antibody by site-specific attachment of the molecules to nucleotide affinity site or sites contained on the antibody molecule or by attachment of the molecules to a nucleotide photoaffinity compound which has been photoinserted at said nucleotide affinity site.

It is a more specific object of the invention to provide methods for site-specifically photoaffinity coupling a purine, azidopurine or similar heterocyclic base containing compound, in particular an ATP- GTP-analog photoaffinity compound, which compound is attached to one or more molecules having a desired activity, to a site or sites contained on the antibody molecule having high affinity for purine, azidopurine or other similar heterocyclic bases, or to preferably an ATP- or GTP-analog photoaffinity compound, which as been photoinserted onto said site or sites.

It is another object of the invention to provide antibodies conjugated to desired molecules, in particular, effector or reporter molecules wherein such molecules are site-specifically attached to the antibody via a nucleotide affinity site, or to a nucleotide photoaffinity analog attached to said site.

It is a more specific object of the invention to provide antibodies conjugated to desired molecules, in particular, reporter or effector moieties wherein such ligands are attached to the antibody at a site having high affinity for purine, azidopurine and other similar heterocyclic bases, in particular ATP- or GTP-analog photoaffinity compounds, or to a nucleotide photoaffinity compound attached to said site.

It is another object of the invention to provide a method for photoaffinity labeling of antibodies by the attachment of nucleotide or nucleoside photoaffinity probes to a nucleotide affinity site or sites contained on the immunoglobulin molecule.

It is a more specific object of the invention to provide a method for photoaffinity labeling of antibodies by the attachment of a labeled purine, azidopurine or other similar heterocyclic base containing photoaffinity probe, and in particular an ATP- or GTP-analog photoaffinity labeled compound to a site or sites on the antibody having high affinity of purine, azidopurine and/or similar heterocyclic bases, and in particular ATP- or GTP-analog photoaffinity compounds.

It is another object of the invention to provide photoaffinity labeled antibodies and compositions containing, wherein such antibodies have been coupled to a nucleotide or nucleoside photoaffinity probe via a nucleotide affinity site contained on the antibody molecule.

It is a more specific object of the invention to provide photoaffinity labeled antibodies and compositions containing, wherein such antibodies have been coupled to a labeled purine, azidopurine and/or similar heterocyclic base containing photoaffinity probe, in particular a labeled ATP- or GTP-analog photoaffinity compound, at a site or sites on the antibodies having high affinity for purine, azidopurine and/or heterocyclic bases.

It is another object of the invention to provide improved methods of immunodetection of an antigen, wherein such methods include the detection and/or quantification of antigen-antibody complexes using a labeled antibody wherein the improvement comprises using as the labeled antibody a nucleotide or nucleoside photoaffinity compound labeled antibody, in particular a labeled purine or purine derivative containing compound labeled antibody, and more particularly a labeled ATP- or GTP-analog photoaffinity compound antibody.

It is another object of the invention to provide improved immunotherapeutics, wherein such immunotherapeutics comprise an antibody conjugated or complexed to molecules having therapeutic or cytotoxic activity, wherein the improvement comprises using as the immunoconjugate an antibody which comprises one or more therapeutic or cytotoxic molecules site-specifically attached to the antibody via a nucleotide or nucleoside affinity site on the antibody. In the preferred embodiment, the affinity site will have high affinity for purine derivatives, in particular ATP- or GTP-analog photoaffinity compounds. The present invention further provides methods of using said immunotherapeutics to treat various disease conditions, and as imaging agents.

It is another object of the invention to provide test kits for detection of antigens comprising diagnostically effective amounts of one or more of the following: antibodies, nucleotide photoaffinity probe, preferably an ATP-or GTP-analog photoaffinity compound, reporter, any substrate(s) necessary for the detection of the particular reporter, and diagnostic carriers, and wherein the various moieties may be separate from one another or may be in various forms of attachment.

It is a more specific object of the invention to provide test kits for detection of antigens comprising diagnostically effective amounts of one or more of the following: antibodies, a purine, azidopurine and/or a similar heterocyclic base containing photoaffinity probe, reporter, any substrates necessary for the detection of the reporter and diagnostic carriers, wherein the various moieties may be separate or may be in various forms of attachment.

It is yet another specific object of the invention to attach chelated heavy metals to antibodies, in particular, triphosphate chelated heavy metals such as $^{111}In^{3+}$ by reacting said chelated heavy metals with nucleotide photoaffinity compounds before or after such nucleotide photoaffinity compounds are attached to a nucleotide affinity site or sites contained in an antibody molecule. In the preferred embodiment, the nucleotide photoaffinity compound will comprise a purine, azidopurine and/or a similar heterocyclic base containing compound, and most preferably will comprise ATP- or GTP-analog photoaffinity compounds.

It is yet another specific object of the invention to provide a novel method of attaching nucleic acids to antibodies, e.g., antisense nucleic acids, DNA, RNA or mixtures thereof, comprising attaching said nucleic acids to the antibody molecule using a nucleotide or nucleoside affinity compound, preferably a purine, azidopurine or similar heterocyclic base containing nucleotide affinity compound, more particularly an ATP- or GTP-analog photoaffinity compound which comprises a highly negatively charged phosphate (tri or tetraphosphate) having high affinity for positively charged polylysine.

It is a more specific object of the invention to attach desired molecules, e.g., reporter or effector molecules which contain one or more reactive amino groups, or which have been attached to a spacer comprising one or more reactive amino groups, to an antibody by reacting same with a nucleotide affinity compound having a reactive cis-hydroyl group containing ribose moiety, which cis-hydroyl group may be converted to a dialdehyde under gentle conditions, and wherein such attachment may be effected before or after the nucleotide affinity probe is attached to an antibody via nucleotide affinity site or sites contained on the antibody.

It is another object of the invention to identify protective photoaffinity sites in other proteins, e.g., other immunoglobulin-like proteins based on the presence of amino acid residues similar to those which constitute the subject photoaffinity site.

BRIEF DESCRIPTION OF THE FIGURES

FIG. 12c shows the amino acid sequence of SIC5 |SEQ ID NO.:1| and 8019 |SEQ ID NO.:2| antibodies deduced from cloned and sequenced V genes.

FIG. 13b shows the predicted contacts of the purine ring with residues H101, H103 and L36 of the antibody molecule. The model exemplifies how a photoaffinity probe inserts into a hydrophobic pocket at the bottom of the antigen binding site.

DETAILED DESCRIPTION OF THE PREFERRED EMBODIMENTS OF THE INVENTION

Figure 1:
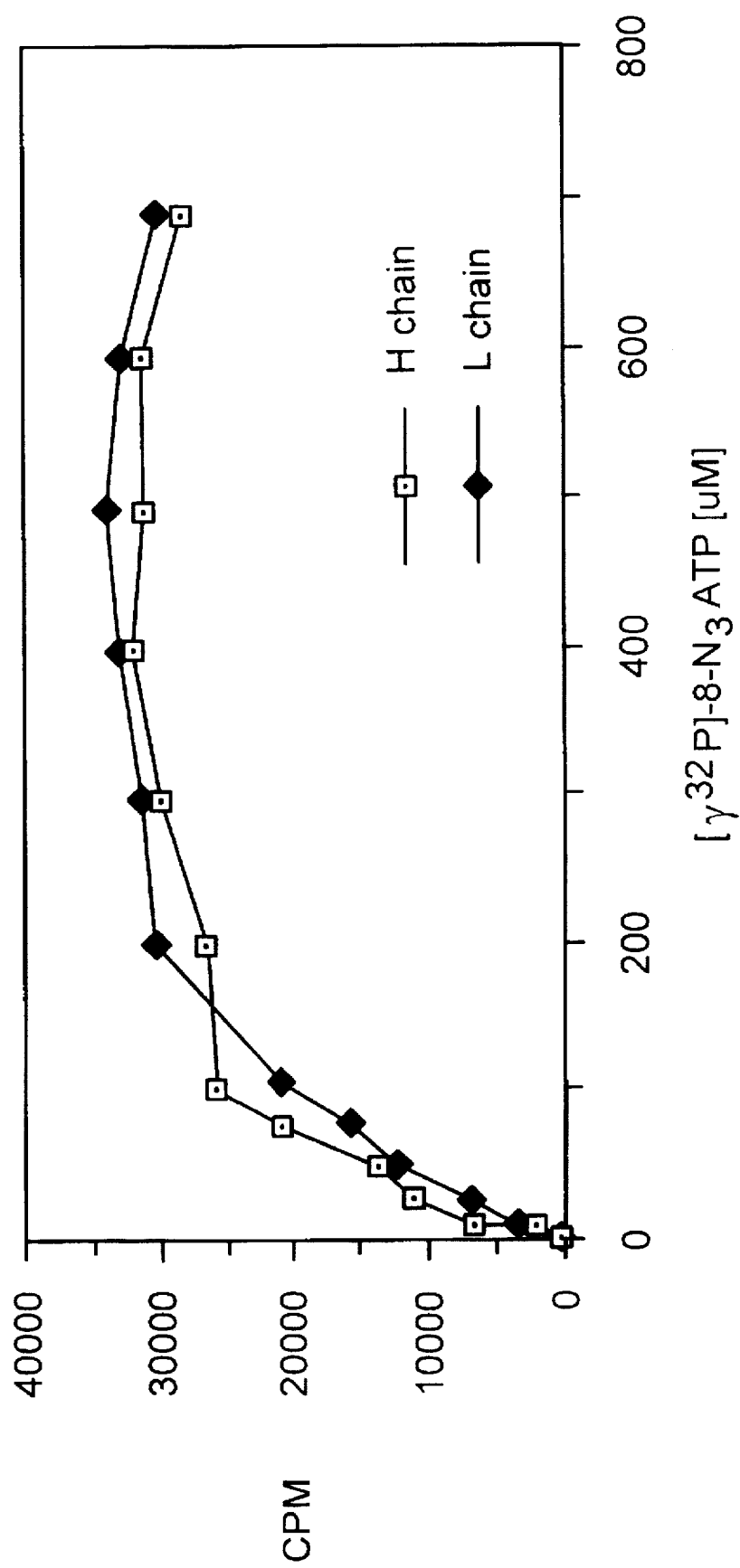
FIG. 1 is a graph which compares the photoincorporation of $[\gamma^{32}P]$-8-$N_3$ ATP into the heavy and light chains of the SIC5 monoclonal antibody wherein the extent of photoincorporation is quantified by liquid scintillation counting. The results show that the radioactive probe covalently attached to both heavy and light chains.

The present invention provides the discovery that some, if not all, antibodies contain one or more photoaffinity sites which provide for the selective site-specific attachment of photoaffinity compounds thereto. In particular, it has been discovered that antibodies comprise one or more sites having high affinity for purines, azido-purines and other similar heterocyclic organic compounds, and specifically ATP- or GTP-analogs. However, the present inventors do not wish to be limited to purine or azidopurine binding sites, since, given the teachings in this application, other photoaffinity binding sites may further be identified, e.g., by reaction of antibodies with non-purine containing photoaffinity compounds, e.g., pyrimidine derivatives such as photoactive analogs of dUTP, including 5-azido-2'-deoxyuridine 5'-triphosphate (5-N$_3$dUTP).

The purine or azidopurine nucleotide affinity site will hereinafter be referred to as the "purine ring binding" or simply the "PRB" domain or site.

The PRB site on antibody molecules was discovered after it was found by the present inventors that photoaffinity compounds, in particular purine or azidopurine photoaffinity compounds readily attach to antibodies and antibody fragments by a photoactivated chemical reaction which occurs under mild, physiological conditions. Specifically, it has been discovered that antibodies comprise one or more PRB sites which exhibit such a high affinity for purines and azidopurine photoaffinity analogs, that reaction of antibodies with purine and azidopurine photoaffinity analogs under mild, physiological conditions, and more particularly after only a single 2–5 minute photolysis results in nearly 100% photoattachment.

This is in contrast to the harsh and potentially damaging conditions which are generally required to facilitate the effective covalent attachment of desired molecules to antibodies. Thus, the present invention provides an improved method for the attachment of desired molecules to antibodies, since it utilizes reaction conditions which are more compatible with the preservation of labile biological molecules and living cells.

However, it should be emphasized that while the conditions which facilitate the attachment of nucleotide photoaffinity compounds to antibodies are inherently gentle, this, in itself, did not ensure a successful outcome. Foremost, prior to the invention, it could not have been predicted with any degree of certainty that this photoaffinity reaction would occur under any conditions, because it was not known that antibodies comprised a site or sites having affinity for photoaffinity compounds, in particular nucleotide and nucleoside photoaffinity compounds, and more particularly sites having high affinity for purine, azidopurine or similar heterocyclic base containing photoaffinity compounds. Moreover, even assuming that the existence such sites had been known, it could not have been predicted that reaction with such sites with compatible photoaffinity compounds would not have adversely affected antibody activity, most especially the ability of the antibody to bind antigen. For example, it was entirely possible that the nucleotide or nucleoside photoaffinity compounds could have inserted in the antibody molecule at a site or sites within or sufficiently proximate to the antigen combining site, such that antigen binding activity was lost or substantially impaired. Alternatively, it was possible that the insertion of the nucleotide or nucleoside photoaffinity compounds into antibody molecules could have induced conformational changes in the antibody molecule causing substantial reduction or loss of other antibody functions. However, quite surprisingly it has been found that nucleotide photoaffinity analogs readily attach to antibodies, in a site-specific manner, under conditions which do not result in substantial loss of antigen binding activity.

Moreover, experiments discussed infra indicate that a novel photoaffinity site is present in the variable Ig domains of antibodies which involves invariant residues and which apparently comprises conserved tryptophan and tyrosine residues. More specifically, this site apparently corresponds to amino acid residues 19–40 of VL and to 88–113 of VH. The site binds nucleotide photoaffinity probes such as 8-azidopurine with high affinity allowing very efficient photomodification under mild conditions. Furthermore, the computer modeled insertion of the ligand into a three-dimensional Fv structure shows that access to the site does not cause steric interference with antigen contacting CDRs. Since the site is an integral part of the Ig structure, insertion of a ligand should not change or distort the overall antibody structure, nor should the ligand impair the antigen binding site. This is substantiated by experiments disclosed infra which demonstrate that affinity modified antibodies produced according to the invention retain full antigen binding. This indicates that this site which is apparently conserved in different antibody molecules is uniquely suitable for tethering desired molecules such as diagnostic and therapeutic agents to the Fv region of antibodies by photoaffinity linkers.

Thus, the invention in general provides a novel means for site-specifically photoattaching desired molecules to antibodies by photoattachment to nucleotide or nucleoside photoaffinity sites contained in antibody molecules. The invention further provides general methods for studying the function of these nucleotide and nucleoside affinity sites, by binding different nucleotide and nucleoside photoaffinity compounds to these sites and evaluating their effects on antibody functions, e.g., effector functions.

As discussed in the Background of the Invention, methods for photoinsertion of nucleotide photoaffinity compounds, and specifically purine and purine analog photoaffinity compounds in proteins having specific nucleotide binding sites have been reported in the literature. The subject invention embraces any set of reaction conditions which provides for the effective photoinsertion of a nucleotide or nucleoside photoaffinity compound, preferably a purine, azidopurine or similar heterocyclic base containing photoaffinity analog, and most preferably an ATP- or GTP-analog photoaffinity compound, into an antibody molecule, which does not result in substantial loss of antigen binding.

Suitable methods for attaching nucleotide photoaffinity analogs to proteins are described, e.g., in Potter & Haley,

*Meth. in Enzymol.*, 91:613–633 (1983); Owens & Haley, *J. Biol. Chem.*, 259:14843–14848 (1987); Atherton et al. *Biol. of Reprod.*, 32:155–171 (1985); Khatoon et al. *Ann. of Neurology*, 26:210–219 (1989); King et al. *J. Biol. Chem.*, 269:10210–10218 (1989); Dholakia et al. *J. Biol. Chem.*, 264:20638–20642 (1989); Campbell et al. *Proc. Natl. Acad. Sci. U.S.A.*, 87:1243–1246 (1990); and Kim et al. *J. Biol. Chem.*, 265:3636–3641 (1990), which references are incorporated by reference in their entirety herein.

Any antibody or antibody containing composition which effectively binds nucleotide or nucleoside photoaffinity compounds is within the scope of the present invention. This includes by way of example, polyclonal and monoclonal antibodies, recombinant antibodies, chimeric antibodies, humanized antibodies, bispecific antibodies, single chain antibodies, antibodies from different species (e.g., mouse, goat, rabbit, human, rat, bovine, etc.), anti-idiotypic antibodies, antibodies of different isotype (IgG, IgM, IgE, IgA, etc.), as well as fragments and derivatives thereof (e.g., $(Fab)_2$, Fab, Fv, Fab, 2(Fab), Fab', $(Fab')_2$ fragments).

Optimal reaction conditions will vary dependent upon factors including the concentration of antibodies in the particular composition, the isotype and/or species origin of such antibodnucleotide o number and affinity of nucleotide or nucleoside binding sites present on the particular antibodies. Suitable conditions can readily be determined by the skilled artisan by reference to the above-cited publications relating to nucleotide photoaffinity labeling of proteins, and the examples therein.

The invention further embraces the use of any nucleotide or nucleoside photoaffinity compounds which effectively photoinserts into one or more nucleotide affinity sites of a selected antibody under conditions which provide for the substantial retention of antigen binding activity. Moreover, if the antibody is to be used as a therapeutic agent, such conditions would ideally preserve other antibody functions, e.g., effector functions, comprised in the Fc portion of the antibody molecule (e.g., complement activation).

The particular nucleotide or nucleoside photoaffinity compound may be directly reacted with an antibody, or it may first be attached to another compound, e.g., a molecule having a desired effector function or a reporter molecule, e.g., a radioactive label.

Many nucleotide photoaffinity probes may be synthesized and used successfully. The photoaffinity compounds of the invention will preferably comprise adenine analogs, although guanine analogs can be substituted therefor. For example, purine binding sites may be effectively labeled by the following, and their 5'-mono-, di- and triphosphates: oligomers of a single azidoadenylyl species, such as, for example: 2-azido or 2-azidoadenylyl(2'-5')2-azidoadenylyl(2'-5')2-azidoadenosin e; 2-azido or 8-azidoadadenosine; 8-azidoadenylyl(2'-5')-8-azidoadenylyl(2'-5')8-azidoadenosine; 8-azidoadenylyl(2'-5')8-azidoadenylyl(2'-5')8-azidoadenylyl-(2'-5')8-azidoadenosine; 2,8-diazidoadenylyl(2'-5')2,8-diazidoadenylyl(2'-5')2,8-diazido-adenosine; 2,8-diazidoadenylyl(2'-5')2,8-diazidoadenylyl(2'-5')2,8-diazidoadenylyl(2'-5')2,8-diazidoadenosine; also oligomers of AMP and a single azidoadenylyl species, such as, for example: 2-azidoadenylyl(2'-5')2-(2'-5')adenosine; adenylyl(2'-5')8-azido-adenylyl(2'-5')8-azidoadenosine; also oligomers containing more than one azidoadenylyl species, such as, for example: 2-azido-adenylyl(2'-5')8-azidoadenylyl(2'-5')2-azidoadenosine; also oligomers resulting from any combination of the monomers AMP, 2-azido-AMP, 8-azido-AMP and./or 2,8-diazido-AMP, provided that at least one such monomer incorporated into the oligomer is an azido-AMP species.

In addition photoaffinity compounds of the invention may also include photoactive coenzyme analogs of $NAD^+$, exemplified by nicotinamide 2-azidoadenosine dinucleotide (2-azido-$NAD^+$), or analogs of NADH, exemplified by nicotinamide 2-hydrazidoadenosine dinucleotide (2-azido-NADH).

Alternatively, guanine moieties can be contained in each of the exemplary compounds in place of the respective adenine moieties. Preferred compounds of the present invention will be synthesized from azidoguanosine 5'-triphosphates or combinations thereof, or from azidoguanosine 5'-triphosphates and ATP. The latter provides a (2'-5') oligomer containing both guanylyl and azidoguanylyl moieties.

Furthermore, photoaffinity compounds of the present invention may also include, for example, pyrimidine derivatives. For instance, photoactive analogs of dUTP, such as 5-azido-2'-deoxyuridine 5'-triphosphate (5-$N_3$dUTP), may be synthesized from dUMP and provide a pathway for the synthesis of other useful 5-substituted uridine nucleotides. The 5-diazouridine nucleotides may, for example, serve as active-site-directed photoaffinity probes or as substrates for polymerizing enzymes to generate additional photoactive nucleic acids which remain stable to extremes of pH and which remain effective photolabeling reagents in the presence of reducing agents. Moreover, since the synthesis of 5-$N_3$dUTP employs mild conditions, it is also possible to synthesize homopolymers of 5-$N_3$dUTP to provide single-stranded photoactive DNA of defined length. Using 5$N_3$UTP one can similarly produce photoactive RNA.

Generalized methods for the synthesis of aryl azides include nucleophilic displacement of a bromine, chlorine or nitro group by an azide ion or the addition of sodium azide to an acidic solution containing a diazotized primary aromatic amine.

To date the most widely used 8-azidopurine is probably 8$N_3$cAMP. One of the advantages of 8$N_3$cAMP is that in mammalian systems there are only two types of proteins that are known to bind cAMP with high affinity, the cAMP phosphodiesterases and the regulatory subunits of the cAMP-dependent protein kinases. The photoprobes [$^{32}$P]8$N_3$cAMP and [$^{32}$P]8$N_3$ATP have been employed to study, for example, the mechanisms of action of cAMP-dependent protein kinase. Photoactive analogs of GTP, e.g., [$^{32}$P]8$N_3$GTP, have been developed to study, for example, tubulin polymerization, while photoactive analogs of UTP, e.g., [$^{32}$P]5$N_3$dUTP have been generated to study, for example, the binding site of DNA binding proteins.

Preferred compounds of the present invention are synthesized from azidoadenosine 5'-triphosphates or combinations thereof, which provide a (2'-5')oligomer containing both adenylyl and azidoadenylyl moieties. Especially preferred photoaffinity compounds for use in the present invention include in particular 2-azido-ATP, 8-azido-ATP benzophenone-ATP or other compounds which effectively compete with 2 or 8-azido-ATP for occupancy of the PRB binding domain.

As noted, these photoaffinity compounds may further be attached to other molecules, e.g., effector molecules or reporter molecules, provided that such molecules do not adversely affect the ability of the photoaffinity compound to effectively photoinsert into nucleotide binding site or sites contained in the particular antibody, or provided that such molecules may be effectively attached to a nucleotide or nucleoside photoaffinity compound which has been bound to the particular antibody.

Nonradioactive reporter molecules or labels can be divided into two categories: (i) chromogenic, fluorogenic, or chemiluminescent dyes or (ii) ligands. Dyes are normally of from 8 to 40 carbon atoms, preferably from 9 to 30 carbon atoms. The dyes further normally contain from 1 to 10 heteroatoms usually oxygen, nitrogen, or sulfur, and normally contain no halogen atoms or up to 10 halogen atoms usually iodine, bromine, chlorine, or fluorine. Chromogenic dyes may include phenol sulfonephthalein and analogs of tetrazolium.

Fluorogenic dyes may include fluorescein isothiocyanate, dichlorotriazinylamino fluorescein, morpholinorhodamine isothiocyanate, tetramethylrhodamine isothiocyanate, and 4-acetamido-4-isothiocyanostilbene-2 with 2'-disulfonic acid. Fluorescent purine derivatives may also include, for example, the fluorescent GTP analog 2'3'-O-(2,4,6-trinitrocyclohexadienyl-idine)guanosine 5'-triphosphate (TNP-GTP), or the equivalent fluorescent ATP derivative (TNP-ATP).

Chemiluminescent dyes may include 5-amino-2,3-dihydrophthalazine-1,4-dione (luminol), derivatives of isoluminol and acridinium esters.

Any ligand may be employed for which an appropriate receptor may be found to have satisfactory specificity for the ligand.

Various methods or protocols may be employed in measuring the amount of the labels. These protocols can include for example, radioimmunoassay (RIA), immunoradiometric assay (IRMA), sandwich IRMA, fluoroimmunoassay (FIA), chemiluminescent assays, bioluminescent assays, and enzyme linked immunosorbent assays (ELISA) among others.

The labeled probe of the present invention can be used in any conventional hybridization technique. Hybridization formats which may be useful in the practice of the present invention include those in which the sample is immobilized on a solid support (solid-phase hybridization) and those wherein the species are all in soLution (solution hybridization). Solution hybridization is preferred in the present method. Another method of interest is the sandwich hybridization technique.

Certain factors are considered when a unique biochemical macromolecular marker is identified by means of a radioactive photoaffinity label, as is the preferred method of the present invention. For example, consideration should be given to: (a) temperature of incubation and photolysis, (b) length of incubation and photolysis, (c) concentration of photoaffinity reagent, (d) binding affinity of protein for the reagent and natural ligands, (e) stability of the photoaffinity reagent in each particular system, (f) ionic strength, pH, co-factors, (g) protein concentration, (h) intensity of photolyzing light, (i) quenching of reaction and separation of unused label, and (j) interpretation of results. Potter & Haley in *Meth. in Enzymol.*, 91:613–633 (1983) provide a detailed account of preferred procedures for labeling a specific biochemical marker macromolecule in a sample with a photosensitive purine triphosphate azide analog.

Temperature of the photolysis reaction between the antibody sample and the selected photoaffinity label can range from 0° C. to room temperature (25° C.) or above. However, the exchange rate between bound and unbound cAMP or 8-$N_3$cAMP approaches negligible levels at 0° C., and is greatly increased at room temperature. Conversely, once 8-$N_3$cAMP is bound to the specific macromolecular marker, it may be cold trapped onto the protein by dropping the temperature to nearly 0° C. Therefore, the most preferred procedure includes preincubation of the components at room temperature, and photolysis in plates set on ice to reduce the temperature to approximately 0° to 4° C. By the present invention, the antibody containing sample is preferably incubated at room temperature with the radioactive photoaffinity probe for approximately 0.5 to 1.0 minutes. Most preferably the mixture is vortexed for 6 seconds followed by an additional 24 seconds of mixing, immediately followed by placing the sample on ice for photoactivation.

The concentration of photoaffinity reagent must be compatible with the binding affinity of the antibody which is to be labeled. Excessively high concentrations, however, can lead to undesirable nonspecific labeling which increases linearly with concentration. Best results can be obtained by experimentally determining the optimum concentration for photoincorporation. Directly related to the determination of concentration is the stability of the reagent. The stability of the reagent can be determined by thin-layer chromatography, e.g., by fluorescent cellulose thin-layer chromatography.

Ionic strength, pH, cofactor, and metal ion concentrations can each affect antibody structure, and are readily adjusted by those skilled in the art to achieve optimal labeling conditions. The higher the protein content of the sample, the denser the solution becomes to light. Therefore, in a denser solution, less UV light reaches the photoreagent per unit of time, decreasing the rate of photoincorporation. Aggregation of the protein can also affect the binding time of the reagent to the protein, thereby increasing or decreasing photoincorporation. One must experimentally redetermine optimal photolysis time when changing protein concentration if maximum incorporation of the photolabel is desired.

Detection of the labeled antibody occurs following an appropriate, predetermined incubation time to effect a reaction, and is calculated on the basis of the antibody sample and the selected photoaffinity probe.

The intensity of the photolyzing light is such that maximum photoincorporation can be obtained in a minimum amount of time without appreciable change in temperature or damage to the biological sample. Preferably the photolysis is achieved at 254 nm with an ultraviolet light source.

Ultraviolet (UV) light is essential for the activation of the photoprobe treated samples, but only a low intensity UV light is necessary. The intensity of the UV light can range from 180 to 800 $\mu W/cm^2$ by conventional sources to 4000 $\mu W/cm^2$ and above when a high intensity source is used to achieve rapid photolysis.

Photolysis times range from 15 seconds to 5 minutes and must be experimentally determined for each reaction system. For lamps having intensities of 180–800 $\mu W/cm^2$, the preferred photolysis time ranges from approximately 30 to 120 seconds, most preferably, photolysis is effected in approximately 30 to 60 seconds.

The distance of the light source from the sample is a determinative factor in the conditions of photolysis. A preferred method of the present invention uses an ultraviolet light source having sufficient intensity, about 6200 $\mu W/cm^2$, positioned at a set distance, about 1 cm from the sample, for a time sufficient to effect photoactivation, generally approximately 45 seconds.

The labeled macromolecule is typically separated from the solution containing excess unbound sample and/or label by precipitation, although other recognized methods of protein purification are possible. Recognized methods of precipitation include, but are no limited to addition of an effective protein precipitating agent, such as trichloroacetic acid (TCA), perchloric acid (PCA), acetone, ammonium sulfate polyethylene-glycol (PEG) or the like to the sample. PCA or ammonium sulfate are the preferred precipitating agents in the present method, and PCA is the particularly preferred precipitating agent.

The amount of precipitating agent is determined by the concentration of protein in the sample. The preferred concentration of the precipitating agent is that concentration which effectively precipitates the specific antibody from solution. The most preferred concentration of the precipitating agent is that amount which effectively precipitates the previously activated, photolabeled antibody sample.

The precipitating agent can be mixed with the sample as a dry batch addition or in a calculated equivalent liquid form. The required mixing time may vary with the nature of the agent selected and the size or concentration of the sample. However, the time required is that point after which essentially no additional protein is precipitated from the sample solution at the temperature selected.

The precipitated antibodies may be separated from solution by any effective means, such as centrifugation, sedimentation or filtration. A preferred method of separation of the precipitated protein from the solution is by centrifugation at a sufficient speed and for a sufficient time to effectively isolate the antibody proteins into a pellet, for example by centrifugation. However, the parameters vary with the nature of the antibody solution.

To determine the effectiveness of the precipitation and separation procedures, both the pellet and the supernatant fluid are analyzed for protein content.

The precipitated protein may be solubilized and any remaining reaction quenched by any effective, known method. The determination of the solubilizing agent would depend on the ultimate method of identifying the specific nucleotide binding protein. Therefore, such agents could include, e.g., sodium dodecyl sulfate (SDS) or urea, and certain stabilizing agents.

Any azide remaining after photolysis may be destroyed by the addition of dithiothreitol or its equivalent, and potential phosphotransfer from the triphosphate derivative $N_3ATP$ or $N_3GTP$ may be inhibited by chelators such as EDTA. The preferred protein solubilizing agent is a detergent, particularly SDS, most preferably in a protein solubilizing mix (PSM), such as described by Potter & Haley in *Meth. in Enzymol.*, 91:613–633 (1983) or by procedures standard to most published procedures. A particularly preferred concentration of SDS in the mix is 10%, resulting in a concentration of SDS to the final sample of 4%.

Solubilization can occur either at 0° C. or at higher temperatures without affecting the results. However, solubilization in the present invention is effective at room temperature.

Upon solubilization, the protein sample is applied to a suitable support for separation of the protein fractions. Support materials could include, e.g., polyacrylamide gels, filter paper, starch gels or blocks, cellulose or polyurethane foam. Any effective, known method of protein separation may be used, but preferably separation is by electrophoresis over denaturing or nondenaturing gels, or over a gradient of either type. In the present method, protein separation is usually by electrophoresis on a denaturing gel.

The nature of the sample and the size of the specific nucleotide binding protein determine the concentration of the gel used, which in turn determines the time for separation and the electrical current which must be applied to best achieve protein separation. The protein fractions of the present invention most preferably may be separated by electrophoresis on an SDS-polyacrylamide gel (SDS-PAGE) or by isoelectric focusing (IEF) or on two dimensional systems (IEF×SDS-PAGE). Typically, the sample is fractionated on a 10% polyacrylamide gel, run over a period of 2½ to 3 hours, with constant amperage of 35 mA and an initial voltage of about 140 volts. Any standard electrophoresis equipment can be utilized.

The resultant gels are exposed to X-ray film and visualized by autoradiography according to methods well known in the art. The gels can also be stained to determine the presence of the unique specific protein band or to ascertain that differences in the amount of photolabel incorporation are not due to drastic changes in the protein levels. Many known protein staining methods are widely recognized, e.g., Coomassie Brilliant Blue (CBB) or silver staining. CBB is a commonly used stain that detects proteins based on a hydrophobic interaction between the proteins and the dye. Although any available staining method can be used which effectively distinguishes the specific nucleotide binding protein, CBB is the fastest and most economical for the present method.

Most preferably, each completed SDS-PAGE gel is stained with an effective amount of CBB to stain the selected protein fragments. However, many times proteins can be detected by photolabelling that cannot be detected by any protein staining procedure. In particular, the completed gel is immersed in a 10% CBB (w/v) solution for about 1 hour. Then the gel is destained in a solution to effectively remove excess stain. Particularly preferred is a destaining solution of 5% acetic acid and 10% isopropyl alcohol applied for 10–18 hours.

Finally, the specific binding protein fragments may be visualized by standard autoradiography techniques. The use of an intensifying screen effectively accelerates the visualization process of autoradiography. By the method of the present invention, the stained gel is dried, and then exposed to DuPont Cronex 4 X-ray film. The autoradiographic procedure is for variable time periods depending on the specific activity of the probe photoinserted into the proteins of each experimental sample. Alternatively, if maintained at −70° C., the gel can be subjected to autoradiographic procedures while still in the gel state.

The amount of protein, as well as the radioactivity incorporated into each protein, can be quantified by known methods including, but not limited to, densitometric scans of the exposed X-ray film, or of the stained gel, or by liquid scintillation spectrometry of the protein band following excision from the gel.

As discussed supra, another application of the subject affinity labeling method comprises the attachment of desired effector molecules to antibodies, wherein these molecules are site-specifically attached to a photoaffinity site, in particular at a site or sites having high affinity for purine, azidopurine and other similar heterocyclic bases, and more particularly ATP- or GTP-analog photoaffinity compounds. This is an important application of the subject method given that the present method of attachment is site-specific and does not substantially affect the architecture of the antibody molecule or its ability to bind antigen. Therefore, effector molecule containing antibodies produced by this method will bind to a target more effectively, e.g., a tumor cell expressing the corresponding antigen. Moreover, nonspecific binding should be minimized which is highly significant if the antibody-effector conjugate is to be used as a therapeutic agent, since this should minimize systemic toxicity.

The subject method is applicable for site-specifically attaching any effector molecule which, when attached to a nucleotide photoaffinity compound does not adversely affect the ability of the resultant effector-nucleotide photoaffinity compound to site-specifically attach to a nucleic acid binding site comprised on the antibody molecule, or which may be site-specifically attached to a nucleotide photoaffinity compound which has previously been site-specifically bound to a nucleic acid binding site on an antibody.

As noted previously, an effector molecule is broadly defined as any moiety which exhibits a desired functions, e.g., a particular biological or chemical activity. In the preferred embodiment, the effector will comprise an activity which enables the effector-antibody conjugate to be used a therapeutic or as a diagnostic agent, e.g., for treating or visualizing tumors.

Examples of effector molecules within the scope of the invention include by way of example cytotoxic moieties such as enzymatically active toxins and fragments thereof such as diphtheria toxin, Pseudomonas exotoxin, ricin A, abrin A, modeccin A, alpha-sarcin, *Alevrites fordii* proteins, dianthin proteins, *Phytolacca americana* proteins (PAPI, PAPII, PAPIII), *Momardica charantia* inhibitor, carcin, erotin, *Sapanaria officinalis* inhibitor, gelonin, mitogellin, restrictocin, phenomycin, and enomycin, antitumor agents such as daunomycin, daunorubicin, methotrexate, cytokines such as interleukins (IL-1, IL-2, etc.), interferons ($\alpha$ interferon, $\beta$ interferon, $\delta$ interferon), colony stimulating factors, tumor necrosis factors, and lymphotoxins, enzymes, radionuclides, chelating agents, growth factors, polynucleotides (DNA, RNA, antisense DNA or RNA mixtures thereof) heavy metal isotopes, ligands and anti-ligands such as biotin, avidin or streptavidin, as well as other moieties having therapeutic or diagnostic utility.

The effector moieties may be directly attached to the photoaffinity compound, or attachment may be effected using a bifunctional coupling agent. Examples of such reagents include by way of example SPDP, IT, dimethyl adipimidate HCl, active esters such as disuccinimidyl suberate, aldehydes such as glutaraldehyde, bis-azido compounds, bisdiazonium derivatives such as bis-(p-diazonium benzoyl)ethylenediamine, diisocyanates such as tolylene 2,6-diisocyanate, and bis-active fluorine compounds such as 1,5-difluoro-2,4-ditrobenzene.

Particular types of effector molecules considered to have preferred application in the invention include radiolabels and chelating agents, in particular triphosphate chelated heavy metals such as $^{111}In^{3+}$ (which has known application as a diagnostic imaging agent), nucleic acids having utility in gene therapy or antisense therapy, enzymes having diagnostic or therapeutic utility, and toxins.

Effector molecules may be at-ached to the photoaffinity compound, preferably a purine or azidopurine photoaffinity compound and more preferably an ATP- or GTP-analog photoaffinity compound, by various means of attachment. The selection of suitable means of attachment will depend upon the particular effector and functional groups available for covalent attachment or complexation to the particular nucleotide or nucleoside photoaffinity compound. Preferably, such chemical attachment will occur under mild conditions to preserve the activity of the antibody and effector.

For example, proteins may be attached to the subject purine or purine derivative containing photoaffinity probes, and more particularly ATP- and GTP-analog photoaffinity compounds, by converting the cis-hydroyl group on the ribose under gentle conditions to a dialdehyde. The dialdehyde will then form a Schiff's base with amino groups of proteins or other amino group containing compounds.

Also, the subject photolabeled antibodies have been shown to have very high affinity to polylysine because of the presence of a highly negatively charged triphosphate or tetraphosphate. Consequently, this will permit established procedures to be used to couple a polylysine containing polynucleotide, e.g., DNA, RNA or complexes thereof, to the photolabeled antibody. This will further enable the polynucleotide to be site-specifically targeted to an antigen expressing target, e.g., a tumor cell or a site of infection.

Additionally, it has been shown that the subject nucleotide photoaffinity compounds attach under gentle conditions to triphosphate chelated metals, in particular $^{111}In^{3+}$, wherein this reaction may be effected before or after the photoaffinity compound is attached to the antibody. Preferably, the photoaffinity compounds will comprise ATP- or GTP-analog photoaffinity compounds, and most preferably 2-azido-ATP, 8-azido-ATP or benzophenone-ATP. When used in vivo for therapy, the effector-antibody conjugates of the invention will be administered in therapeutically effective amounts. This will of course depend upon factors including the specific disease condition being treated, the condition of the patient, the antigen binding properties of the antibody (affinity, avidity of antibody for antigen), and the particular effector molecule that is attached to the antibody. Particular disease conditions contemplated for treatment include, e.g., cancers, infectious diseases, and genetic disorders.

The subject photoaffinity compound antibody-conjugates will normally be administered parenterally, when possible at the target, e.g., a tumor, a particular organ, or a site of infection.

For parenteral administration these conjugates will be formulated in a unit dosage injectable form (solution, suspension, emulsion) in association with a pharmaceutically acceptable parenteral vehicle. Such vehicles are inherently nontoxic, and non-therapeutic. Examples of such vehicles are water, saline, Ringer's solution, dextrose solution, and 5% human serum albumin. Nonaqueous vehicles such as fixed oils and ethyl oleate may also be used. Liposomes may be used as carriers. The vehicle may contain minor amounts of additives such as substances that enhance isotonicity and chemical stability, e.g., buffers and preservatives. The antibody conjugates will typically be formulated in such vehicles at concentrations of about 1 mg/ml to 10 mg/ml.

The selection of an antibody subclass for therapy will depend upon the nature of the antigen. For example, an IgM may be preferred in situations where the antigen is highly specific for the target and rarely occurs on normal cells. However, where the antigen is also expressed in non-targeted, e.g., normal tissues on IgG antibody may be preferred.

Also, the antibodies may be attached to other molecules by attachment to non-photoaffinity sites if desired. This may be effected before or after photoaffinity reaction. Moreover, because the site which comprises the photoaffinity site has been identified, it should be possible to protect such site prior to reaction.

Also, it may be possible to engineer the subject photoaffinity site into other proteins, e.g., recombinant proteins so as to produce hybrid proteins which may be photolabeled. This may be useful in a diagnostic setting.

Moreover, hybridization probes may potentially be synthesized corresponding to the subject photoaffinity sites in order to identify similar photoaffinity sites in other proteins, e.g., immunoglobulin-like proteins.

The following examples are offered to more further illustrate the nature, but are not to be construed as limiting the scope thereof.

EXAMPLES

Standard procedures and reagents were used in accordance with Maniatis et al (1982) Molecular Cloning: A Laboratory Manual, Cold Spring Harbor Laboratory, New York. Specific techniques for the photoaffinity labeling of specific nucleotide binding sites with purine phosphate azide analogues were used in accordance with Potter & Haley, *Meth. in Enzymol.*, 90:613–633 (1983).

EXAMPLE 1

Labeling Efficiency of $[\gamma^{32}P]$-8-$N_3$ ATP for SIC5 Antibody

The SIC5 antibody comprises an anti-B cell lymphoma idiotype antibody which is useful for evaluating the efficiency of labeling by idiotype solid phase assays and tumor cell binding as well as in tumor imaging. Therefore, given these inherent properties, this antibody was selected to determine labeling efficiency of the subject method.

In particular, 3 µg of SIC5 antibody in 30 mL of photolysis buffer was photolyzed with increasing concentrations of $[\gamma^{32}P]$-8-$N_3$ ATP and then separated by SDS-PAGE. $^{32}P$ incorporation was detected by autoradiography and quantified by scanning on Optical Imaging Acquisition Analysis (Ambis, Inc.). Photoincorporation was quantitatively confirmed by cutting the appropriate band and determining radioactivity by liquid scintillation counting. These results are set forth in FIG. 1. Based upon these results, it can be clearly seen that the radioactive probe is covalently attaching to both antibody heavy and light chains. It can further be seen that there is a defined saturating concentration of probe at about 200 µm for both chains. This saturation plateau provides strong evidence that there exists a unique and limited number of affinity sites of the antibody which are bound by the $[\gamma^{32}P]$-8-$N_3$ ATP compound.

EXAMPLE 2

Determination of the Specificity of the Antibody Nucleic Affinity Site

In order to identify which part of the $[\gamma^{32}P]$-8-$N_3$ ATP probe is binding the antibody, i.e., the specificity of the antibody affinity site, the following experiment was conducted.

Figure 2:
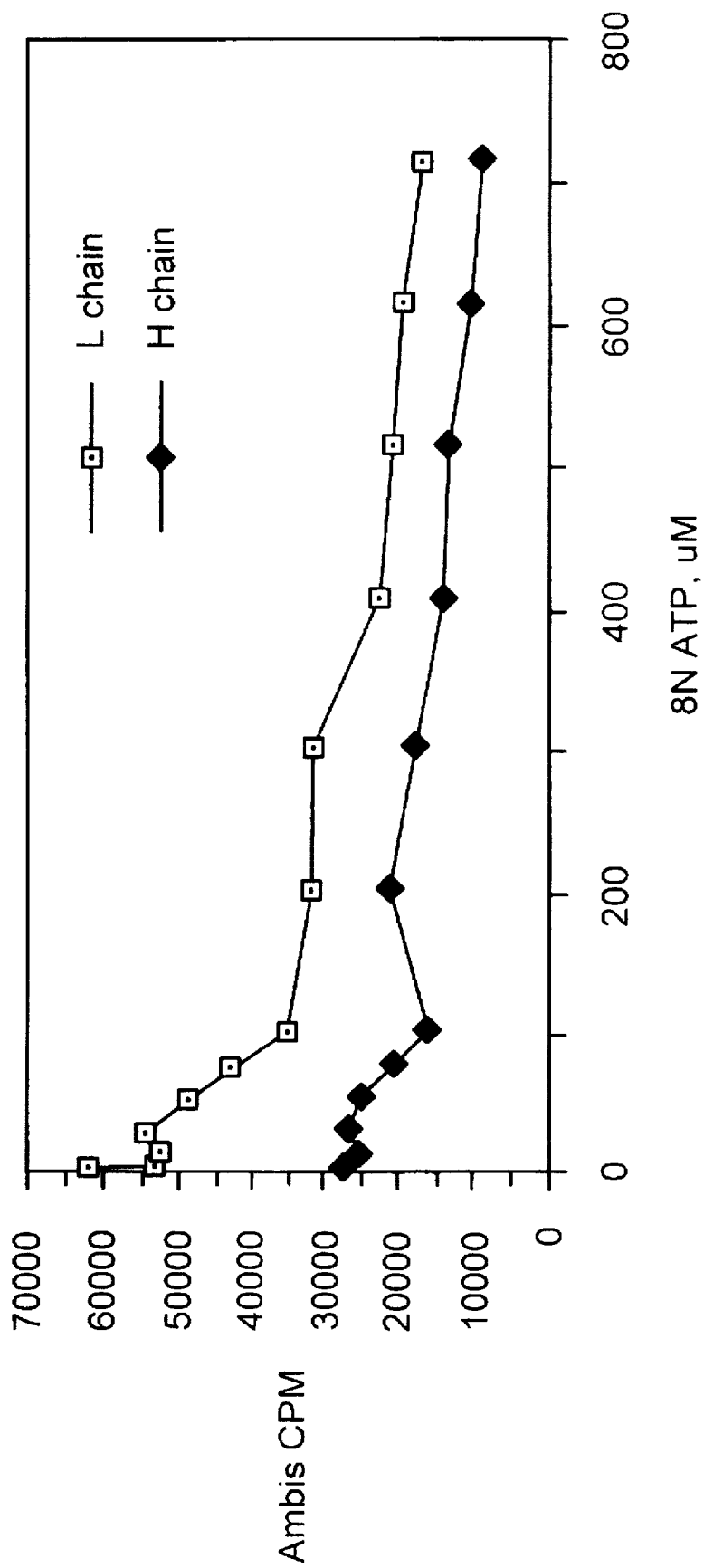
FIG. 2 is a graph which compares the photoincorporation of $[\gamma^{32}P]$-8-$N_3$ATP into the heavy and light chains of the SIC5 monoclonal antibody in the presence of increasing quantities of ATP wherein photoincorporation is quantified by liquid scintillation counting. The results indicate that 50% inhibition occurs at about 350 μM.

The SIC5 antibody was again labeled, but in this example labeling was performed in the presence of increasing amounts of free ATP. Specifically, 3 µg of the SIC5 antibody was photolyzed in the presence of 200 µm $[\gamma^{32}P]$-8-$N_3$ ATP using concentrations of ATP ranging from 0 to 700 µm. The labeled protein was again separated by SDS-PAGE; and radioactivity determined by liquid scintillation counting. These results are shown in FIG. 2.

Based on the results contained therein, it can be clearly seen that ATP inhibits labeling of both the heavy and light antibody chains of the SIC5 antibody. The results further indicate that 50% of inhibition of labeling occurs at around a 350 µm ATP concentration. Thus, these results provide further evidence that the SIC5 antibody comprises one or more sites having specific affinity for the $[\gamma^{32}P]$-8-$N_3$ ATP compound.

EXAMPLE 3

Labeling of the SIC5 Antibody Using $[\gamma^{32}P]$-8-$N_3$ ATP Benzophenone

Another photoactivating probe, $[\gamma^{32}P]$-8-$N_3$ ATP benzophenone, was tested to determine its efficacy for labeling the SIC5 antibody. This experiment was conducted under substantially the same conditions as Example 1, except that $[\gamma^{32}P]$-8-$N_3$ benzophenone was substituted for $[\gamma^{32}P]$-8-$N_3$. Incorporation of label into the SIC5 heavy and light chains were then measured. It was demonstrated that saturation was achieved at about 100 mM concentration of probe.

These results indicate that the SIC5 antibody comprises one or more affinity sites which are effectively labeled by the $[\gamma^{32}P]$-8-$N_3$ ATP benzophenone compound, and that the SIC5 antibody may be effectively labeled using different nucleotide photoactivating probes.

EXAMPLE 4

Affinity of SIC5 Antibody Site for Oligonucleotides

Figure 3:
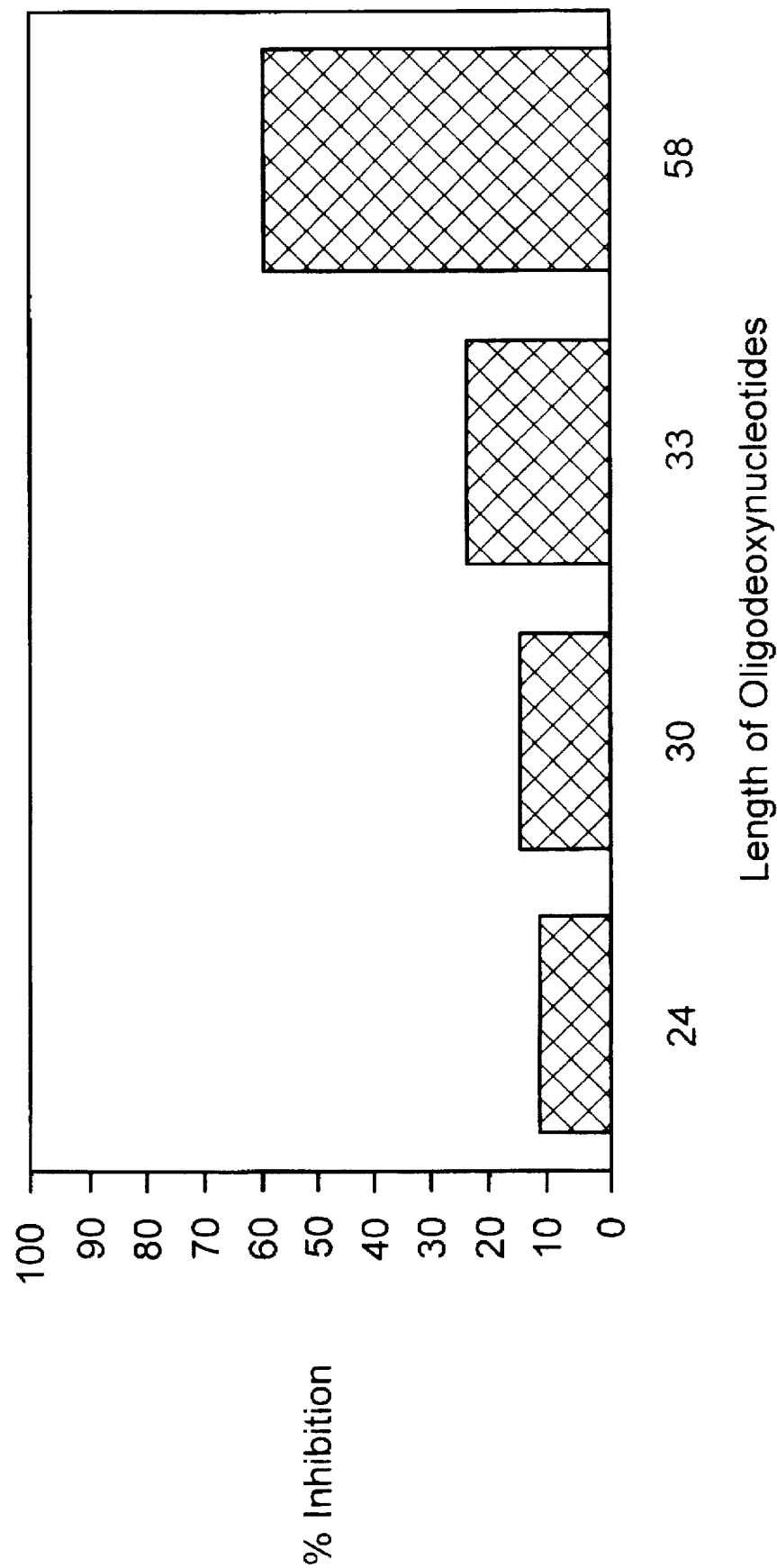
FIG. 3 is a bar graph which compares the percent inhibition of photoincorporation of $[\gamma^{32}P]$-8-$N_3$ATP into the SIC5 monoclonal antibody by oligonucleotides of different lengths, i.e., a 24-mer, a 30-mer, a 33-mer and a 58-mer, wherein photoincorporation is again determined by liquid scintillation counting. The bar graph shows that there is much greater inhibition with larger oligonucleotides.

The affinity of the SIC5 antibody for oligonucleotides was also evaluated using oligonucleotides of different length, to block photolabeling with an ATP probe. Specifically, 3 µg of the SIC5 antibody was incubated for two hours at 4° C. with 1 mg of a 24-mer, 30-mer, 33-mer, 58-mer, followed by incubation with 200 µm of $[\gamma^{32}P]$-8-$N_3$ ATP for 60 seconds, photolysis for 60 seconds, followed by separation of protein using SDS-PAGE. Photoincorporation was again quantitatively determined by cutting the appropriate band and determining $^{32}P$ radioactivity by liquid scintillation counting. These results are contained in FIG. 3. Based on these results, it would appear that blocking efficiency increases with the length of the oligonucleotide. This provides further evidence in support of the existence of one or more sites on the antibody having specific affinity for ATP photoaffinity probes. Additional experiments are planned using oligonucleotides of specific sequences to further analyze the sequence specificity of the affinity site(s).

EXAMPLE 5

Effect of Labeling on Antigen Binding

The effect of labeling on antigen binding and antigen specificity was determined using the 3H1 anti-idiotype antibody, for which an idiotype is readily available. The binding of 3H1 to idiotype was tested in a solid phase binding assay (ELISA) using isotope labeled 3H1 in the presence of unlabeled 3H1 antibody to inhibit binding.

In particular, the idiotype antibody was used as antigen for plate coating (500 mg/well). The same amount of labeled 3H1 (3µg) was mixed with different amounts of the unlabeled antibody and incubated for two hours at 25° C. After incubation, the wells were washed, dried, cut and $^{32}P$ radioactively counted by liquid scintillation. The 5D10 antibody was used as the non-specific cell inhibitor.

Figure 4:
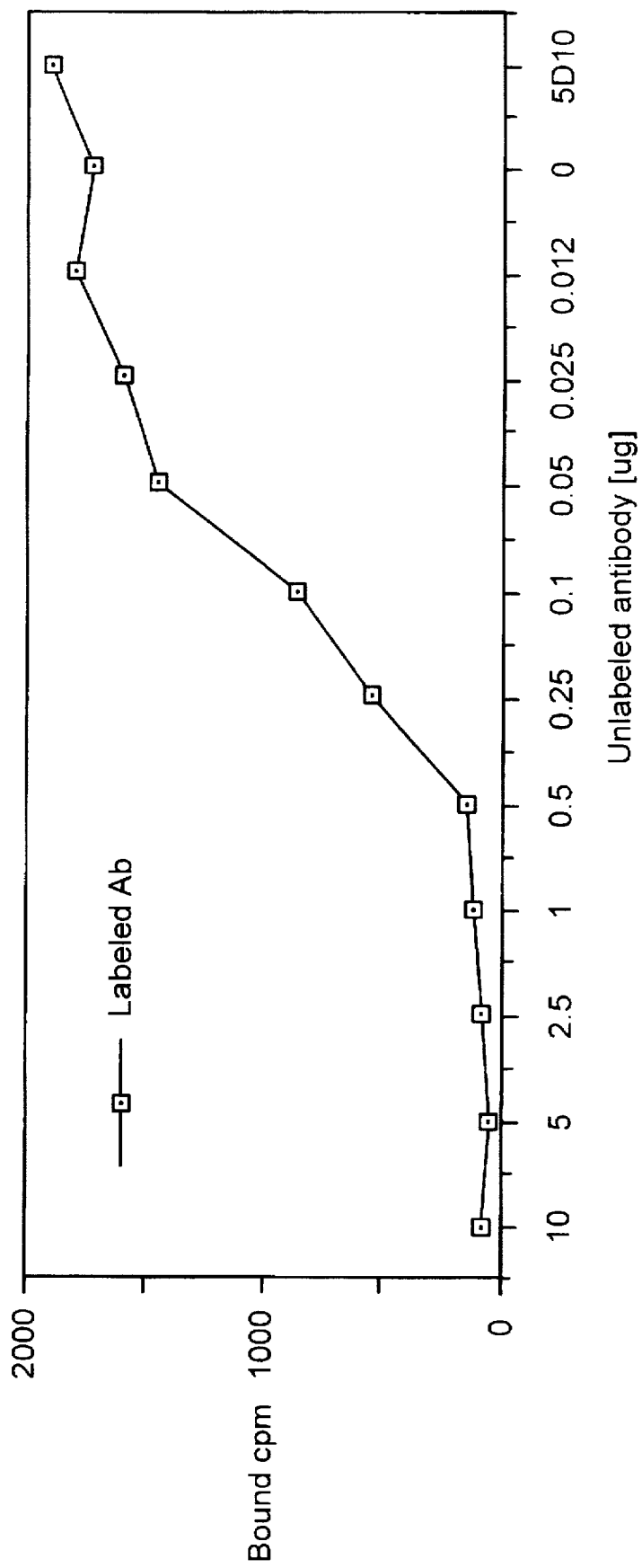
FIG. 4 is a graph of the results of a solid phase binding assay [ELISA] which compares the ability of different amounts of unlabeled 3H1 monoclonal antibody (ranging from 0 to 10 μM) to inhibit binding of the same amount of $[\gamma^{32}P]$-8-$N_3$ATP labeled 3H1 monoclonal antibody to the corresponding idiotypic antibody, and wherein the 5D10 antibody is used as a non-specific cold (unlabeled) inhibitor. Photoincorporation is again quantified by liquid scintillation counting. The results show that cold (unlabeled) 3H1 monoclonal antibody inhibits binding of the labeled 3H1 antibody.

These results, using different specific amounts of unlabeled antibody ranging from 0 to 10 µg are shown in FIG. 4. It can be clearly seen from these results that the cold (unlabeled) 3H1 antibody inhibits the binding of isotope labeled 3H1.

EXAMPLE 6

Cell-Surface Competition Binding of Labeled 5D10 Antibody

The binding of isotope labeled anti-B cell lymphoma idiotypic antibody to live tumor cells was tested. Specifically, $10^6$ SU-DHL-4 cells were incubated with different amounts of unlabeled antibody and the same amount of labeled antibody (3 mg/tube) for 30 minutes at 4° C. Cells were then washed using 20% fetal calf serum (FCS) medium. Binding of $\gamma^{32}$P-labeled antibody was detected by liquid scintillation counting.

Figure 5:
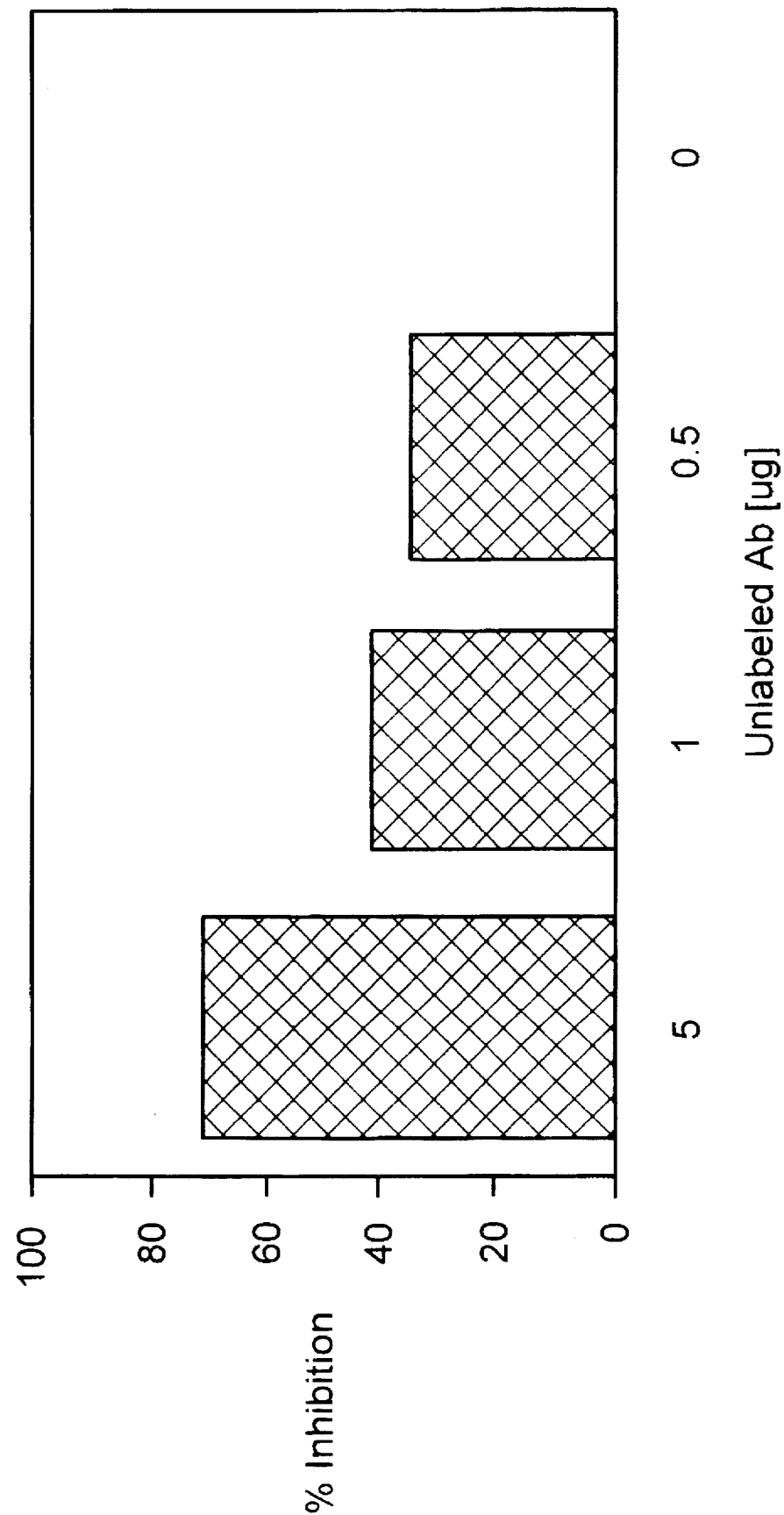
FIG. 5 is a bar graph which compares the ability of different amounts of unlabeled 5D10 monoclonal antibody (5.0, 1.0, 0.5 μg) to inhibit binding of the same amount of $[\gamma^{32}P]$-8-$N_3$ATP labeled 5D10 monoclonal antibody to live DHL4 human lymphoma tumor cells.

These results are contained in FIG. 5. It can be clearly seen that the unlabeled antibody effectively inhibits binding of the isotope labeled antibody to tumor cells.

EXAMPLE 7

Characterization of Labeled Antibodies by Isoelectric Focussing

Figure 6:
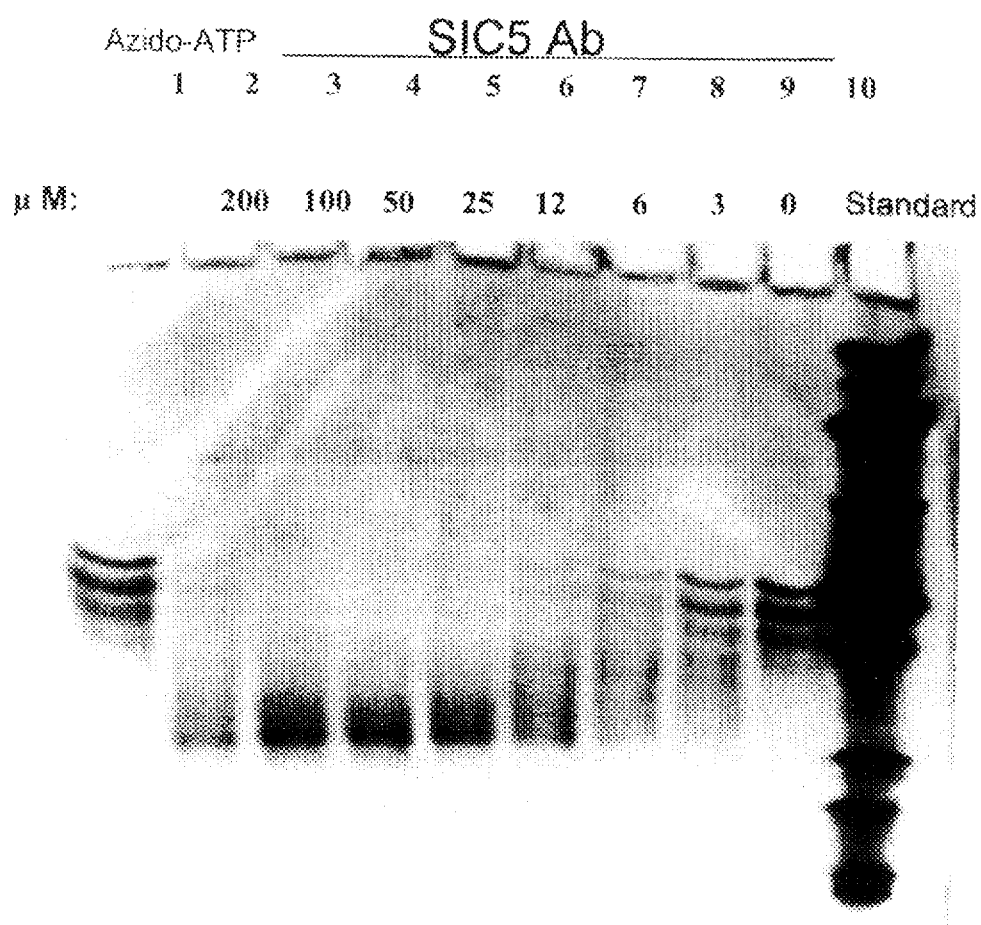
FIG. 6 is a photograph of the isoelectric focussing pattern of unlabeled and $[\gamma^{32}P]$-8-$N_3$ATP labeled SIC5 monoclonal antibody, wherein the SIC5 antibody is photolabeled using increasing concentrations of $[\gamma^{32}P]$-8-$N_3$ATP. The isoelectric focussing standards are A=cytochrome C(pI 9.6), B=equine myoglobin (pI 7.0), C=bovine carbonic anhydrase (pI 6.0), D=phycocyanin (pI 4.65) (lane 10). The unlabeled SIC5 antibody is in lane 1. The $[\gamma^{32}P]$-8-$N_3$ATP labelled SIC5 antibody are as follows: 3.25 μM (lane 9), 6.25 μM (lane 8), 12.5 μm (lane 7), 25 μM (lane 6), 50 μM (lane 5), 100 μM (lane 4), 200 μM (lane 3), 400 μM (lane 2).

Labeled antibodies were also characterized by isoelectric focusing. A representative isoelectric focusing pattern of a labeled and unlabeled antibody is found in FIG. 6.

Isoelectric focusing was effected at a pH ranging from 3 to 10 using S1C5 antibodies which had been photolabeled with increasing concentrations of $[\gamma^{32}P]$-8-$N_3$ ATP. The isoelectric focusing standards used were:

A=cytochrome C (pI 9.6), B=equine myoglobin (pI 7.0), C=bovine carbonic anhydrase (pI 6.0),
D=phycocyanin (pI 4.65) (lane 10).
The unlabeled antibody is shown in lane 1.

S1C5 antibody (5 µg) was photolyzed by 3.125 µm (lane 9), 6.25 µm (lane 8), 12.5 µm (lane 7), 25 µm (lane 6), 50 µm (lane 5), 100 µm (lane 4), 200 µm (lane 3), and 400 µm (lane 2) $[\gamma^{32}P]$-8-$N_3$ ATP.

EXAMPLE 8

Figure 7:
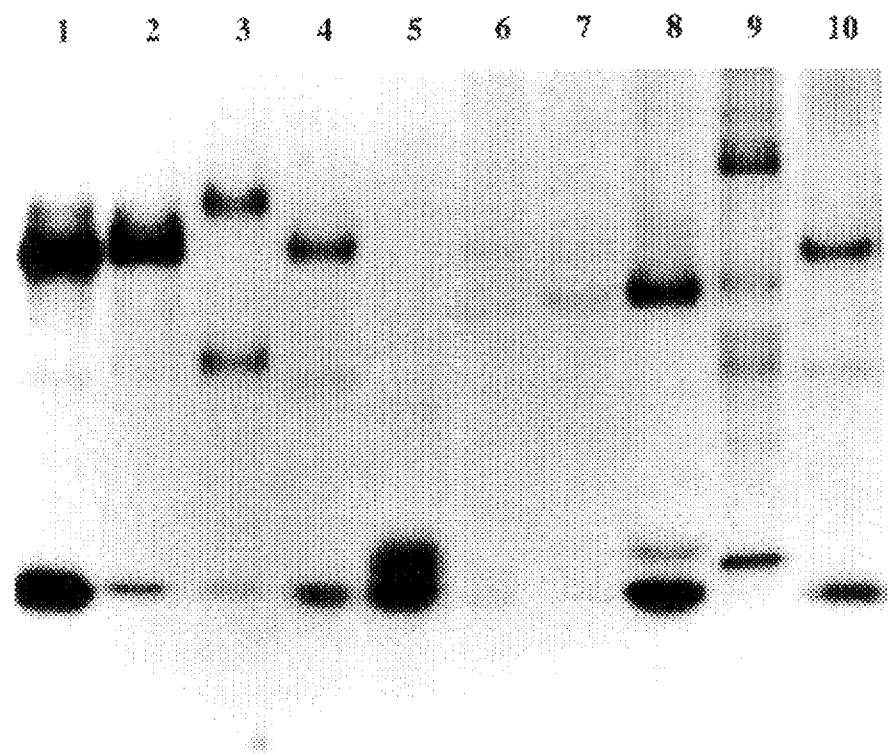
FIG. 7 is a photograph of an autoradiograph made from an SDS- PAGE on which different antibodies which had been photolabeled with $[\gamma^{32}P]$-8-$N_3$ATP were separated. In particular, autoradiograph shows separation of a murine monoclonal IgG1 antibody, 5D10 monoclonal antibody (lane 1), murine myeloma IgG1 (lane 2), murine myeloma IgA (lane 3), goat Ig (lane 4), goat (Fab)₂ fragments (lane 5), human myeloma IgG1K (lane 6), human myeloma IgG1 (lane 7), human myeloma IgM (lane 8), murine monoclonal IgM (lane 9) and murine monoclonal IgG2b, SIC5 (lane 10) which had photolyzed in the presence of 200 μM $[\gamma^{32}P]$-8-$N_3$ATP and were separated by 8–16% gradient SDS-PAGE, stained with Coomassiee Blue, dried and autoradiographed.

Labeling of Antibodies of Different Species and Isotype Using $[\gamma^{32}P]$-8-$N_3$ ATP In this experiment, antibodies of different species, origin and isotype were labeled with $[\gamma^{32}P]$-8-$N_3$ ATP. Specifically, murine, goat, human and rabbit antibodies were labeled with $[\gamma^{32}P]$-8-$N_3$ ATP. Labeling was again effected substantially in accordance with Example 1. The same amount (3 µg) of the respective antibodies [murine monoclonal IgG1, 5D10 (lane 1), murine myeloma IgG1 (lane 2), murine myeloma IgA (lane 3), goat Ig (lane 4), goat (Fab)$_2$ fragments (lane 5), human myeloma IgG1 K (lane 6), human myeloma IgG1 1 (lane 7), human myeloma IgM (lane 8), murine monoclonal IgM (lane 9), murine monoclonal IgG2b, S1C5 (lane 10)] were photolyzed in the presence of 200 µm $[\gamma^{32}P]$-8-$N_3$ ATP and separated by 8-16% gradient SDS-PAGE. Following electrophoresis, the gel was stained with Coomassie Blue, dried and autoradiographed. These results are contained in FIG. 7.

The results indicate that these different antibodies effectively incorporate the label into the heavy and light chains and that the amount of incorporation varies with the different antibodies. It can further be seen that a Fab fragment (goat Ig Fab fragment) is effective labeled.

Thus, these results indicate that nucleotide affinity binding sites suitable for photoaffinity nucleotide labeling are comprised on antibodies of different species, origin and an antibody of different isotype. Moreover, these results indicate that antibody fragments, as well as intact antibodies may be effectively labeled using nucleotide photoaffinity probes.

MATERIALS AND METHODS

The following materials and methods were used in the Examples which follow.
Photoaffinity Labeling Antibodies (3 µg) were incubated with 200 µM $[\gamma^{32}P]$8-$N_3$ATP (5-30 mCi/µmole) in a final volume of 30 µL for 1 minute and photolyzed with a hand-held UV lamp at 254 nm for 1 min. The reactions were quenched with protein solubilizing mixture (10% SDS, 3.6M urea, 162 mM DTT, Pyronin Y and 20 mM Tris, pH 8.0) and analyzed by 6-14% gradient SDS-PAGE. The gels were stained with Coomassie Brilliant Blue, destained, and dried using a slab gel drier. $^{32}$P incorporation was detected by autoradiography and quantified by either scanning on an optical Image and Acquisition Analysis (Ambis, Inc.) or by cutting the appropriate band from the gel counting the radioactivity by liquid scintillation counting.

EXAMPLE 9

Saturation and Protection of Labeling

Antibody S1C5 (Maloney et al, Hybridoma, 4:191-209 (1985)), and 8019 (Koprowsky et al, Somat. Cell. Genet., 5:957-961 (1979)) each (3 µg) were incubated with increasing concentrations of $[\gamma^{32}P]$8-$N_3$ATP for 1 min at 4° C. and photolyzed and analyzed as described above. Protection of photolabeling of S1C5 and 8019 was performed by incubating 34 g of antibodies with increasing concentrations of ATP for 2 min followed by incubation with 200 µM $[\gamma^{32}P]$ 8-$N_3$ATP for 1 min and photolyzed and analyzed as described above. Protection experiments using amino acids were performed by incubating 3 µg of S1C5 antibody with increasing concentrations of amino acids for 2 min, followed by incubation with 200 µM $[\gamma^{32}P]$8-$N_3$ATP for 1 min. Photolysis and analysis were performed as described.
FACS Analysis Tumor cells (38C13 and LS174T, 1×10$^6$) were incubated with biotinylated 8-azidoadenosine labeled antibody S1C5 or 8019 (manuscript submitted) for 60 min. on ice. After washing with 5% FCS/PBS, Neutralite Avidin-FITC (Southern Biotechnology Associates, Inc.) was added and incubated for 30 min., fixed and subjected to flow cytometry. FACS data were generated front a minimum of 9900 cells per sample.
Cloning and Sequencing of VH and VL The genes coding for S1C5 and 8019 antibodies were cloned using standard primers and sequenced as described (Levy et al, Gene, 54:167-173 (1987); Andrea et al, J. Immunol., 144:2614-2617 (1990)). S1C5 was cloned and sequenced by R. Streifer and 8019 by C. C. Meyers (manuscript in preparation).
Tryptic Digestion and Peptide Purification Photolabeled peptides from antibodies S1C5 and 8019 were isolated as follows: Antibodies (2.5 mg) were incubated and photolabeled twice with 425 µM of $[\gamma^{32}P]$8-$N_3$ATP. Photolabeled antibody was precipitated by the addition of 7% PCA and separated from the unbound probe by centrifugation. The pellet was suspended in a solution containing 2M urea, 15.1 mM DTT, and NH$_4$OH (pH 8-9) and incubated at 50° C. for 30 min. Iodoacetamide (235 µM final) was added and the solution was incubated at 25° C. for 30 min. followed by dialysis against 100 mM NH$_4$CO$_3$ for 4 h. The pH of the solution was adjusted to 8-9 and the protein was digested with 60 μg of TPCK-trypsin (Promega) for 18 h. The photomodified were purified by $Al^{3+}$-chelate affinity chromatography (Shoemaker et al. *Biochemistry*, 32:1883–1890 (1993)). The photomodified peptides eluted from the $Al^{3+}$-chelate column were further purified by reversed-phase HPLC using a C8 column (Brownee Labs) on a LKB system equipped with a diode array detector. The mobile system consisted of a 0.1% TFA solution (A) and 0.1% TFA/70% acetonitrile (B) solvent system. The gradient for HPLC was 0–30 min., 0% A; 30–90 min., 0–75% B; 90–95 min., 75–100% B; 95–96 min 100–0% B. Radioactivity associated with the HPLC fractions were determined using a liquid scintillation counter.

Peptide Sequencing and Alignment

HPLC fractions containing photolabeled peptides were sequenced on an Applied Biosystem 477A protein sequencer with an on-line PTH identifications; sequenced tryptic peptides isolated from photolabeled S1C5 and 8019 antibody were aligned with the VL and VH sequences.

Computer Modeling

The crystal structure of IgG Jel103 Fab (PDB code 1MRC) was used to model an Fv fragment. The coordinates in the PDB bank (Bernstein et al. *J. Mol. Biol.*, 112:535–542 (1977)) had a break in between H73–H75. Missing residues were modeled as alanines using the lego-loop options in program O (Jones et al. *Acta Crystollagr.*, A47:110–138 (1991)), and regularized. The coordinates of adenosine-5'-diphosphate were constructed from that of guanosine-5'-diphosphate as observed in the crystal structures of GDP-Jel103 (PDP code 1MRE). The obtained coordinates of ADP were minimized using X-PLOR (Brunger, X-PLOR (version 3.1): A system for X-ray crystallography and NMR (Yale University Press, New Haven, Conn., U.S.A., (1992)). The program CHAIN was used to place the molecule of ADP in the Fv fragment (Sack, *J. Mol. Graphics*, 6:224–225 (1988) ). Pictures were made using the program SETOR (Evans, *Mol. Graphics*, 11:134–138 (1993)). The model was not refined and hence has a number of close contacts between ADP and Fv atoms. Some small rearrangement of the Fv fragment will have to occur in order to relieve the close contacts with the ADP molecule.

EXAMPLE 10

Photoaffinity Labeling of Igs

Figure 8:
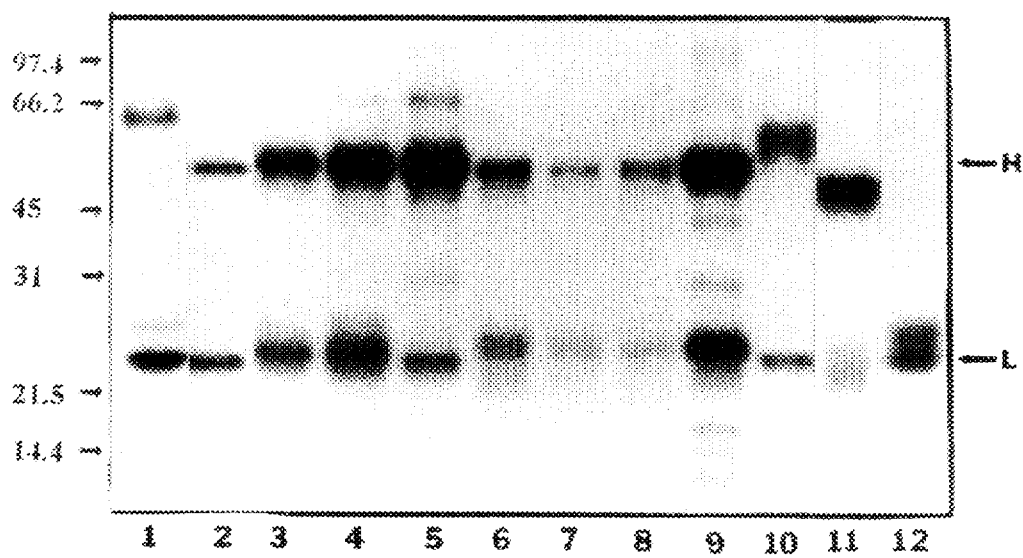
FIG. 8 is an autoradiograph of photoaffinity labeled antibodies. The figure shows light and heavy chains with variable degree of incorporation of the photolabel.
Figure 9A:
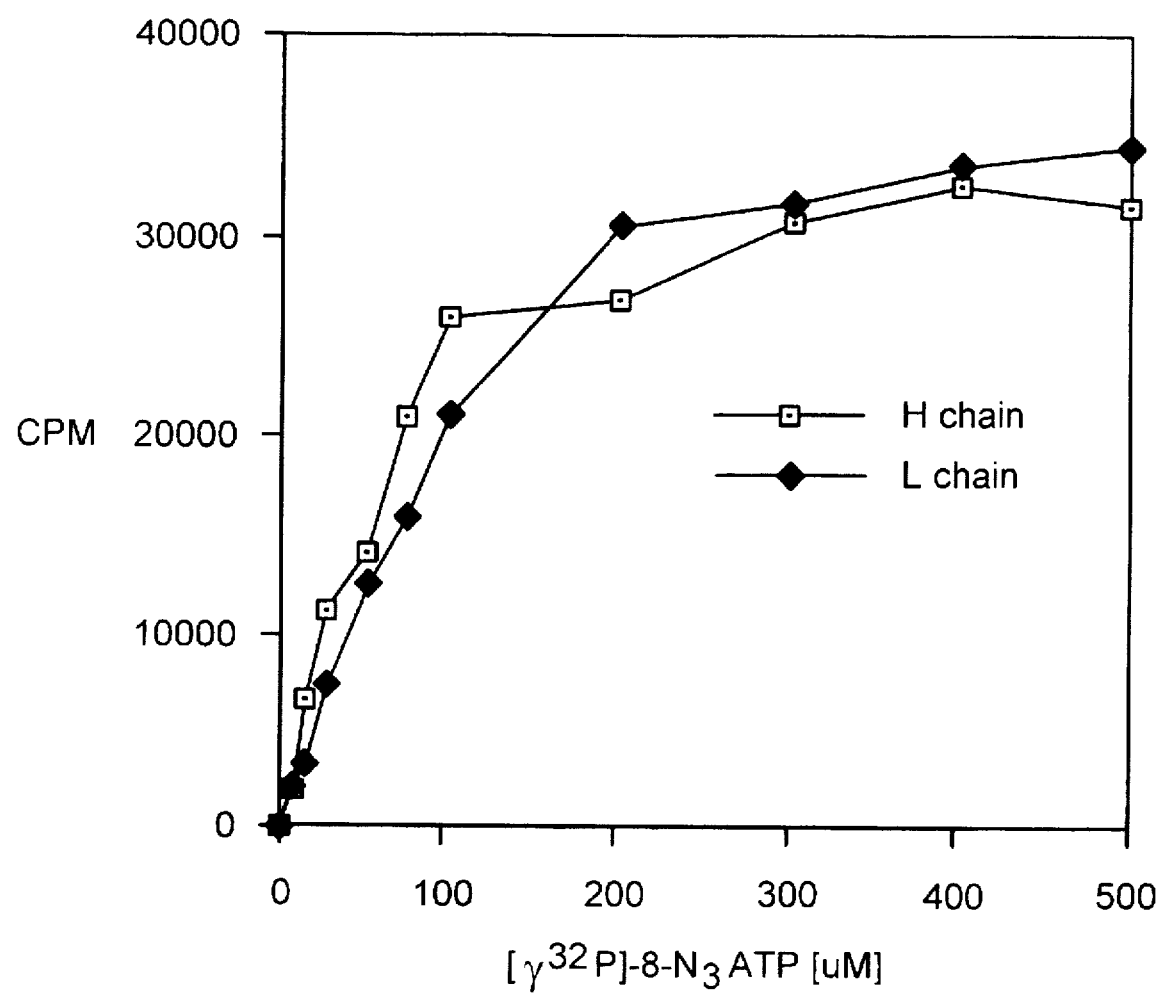
FIGS. 9a–9d shows results of photolabeling experiments using SIC5 and 8019 antibodies labeled with increasing concentrations of $[\gamma^{32}P]$8-$N_3$ATP. The results in FIGS. 9c and 9d show that photolabeling is inhibited by ATP.
Figure 9B:
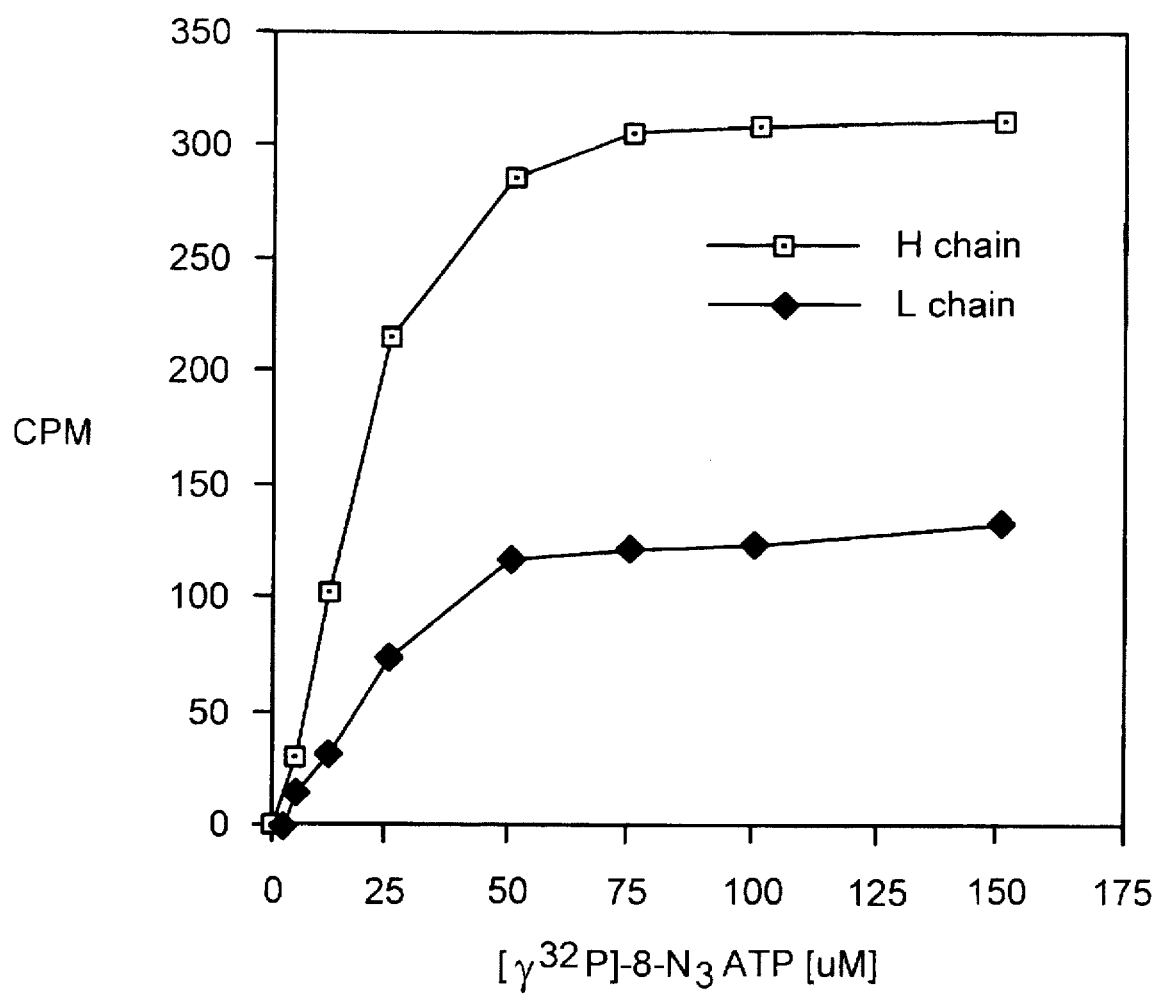
Figure 9C:
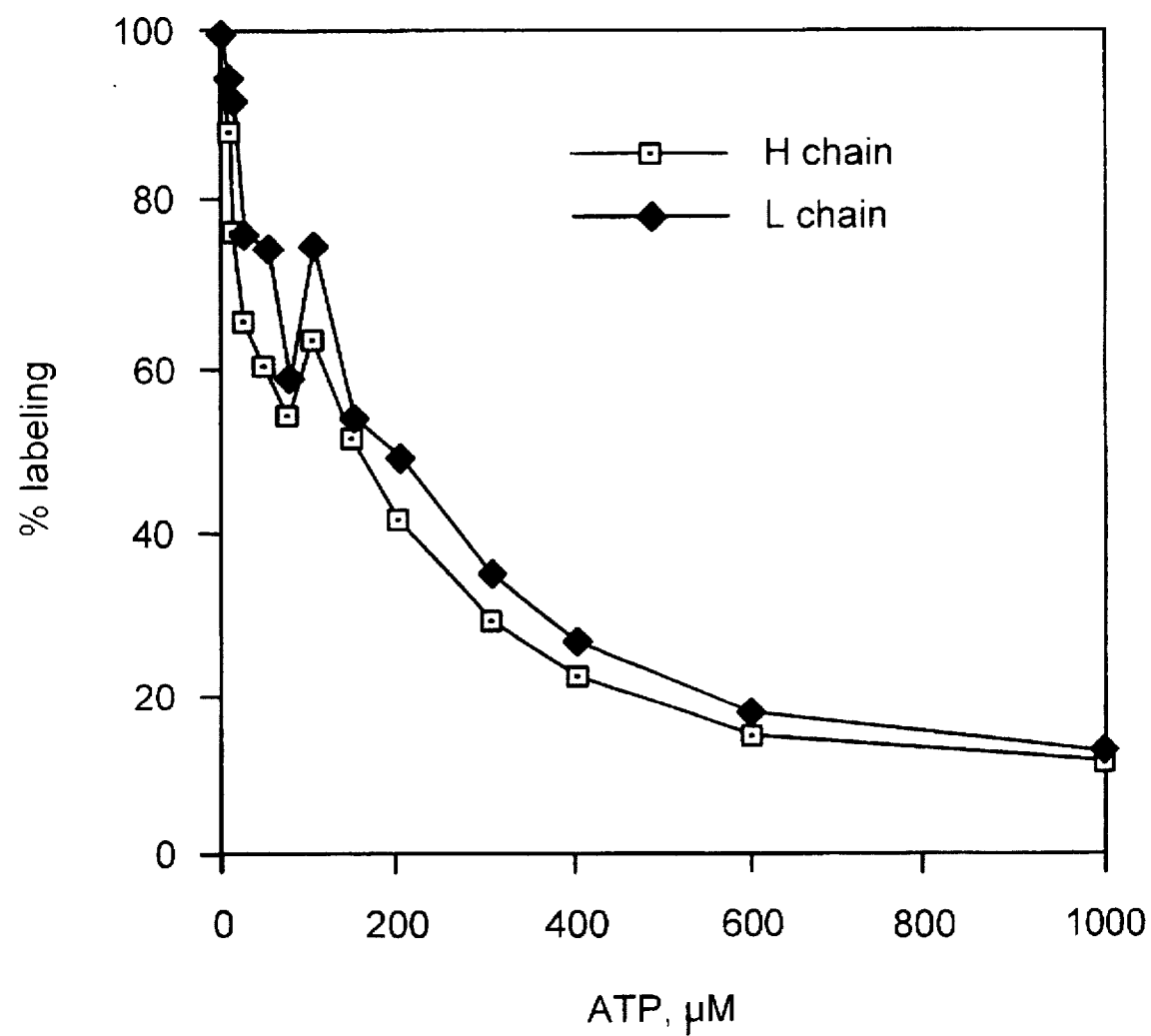
Figure 9D:
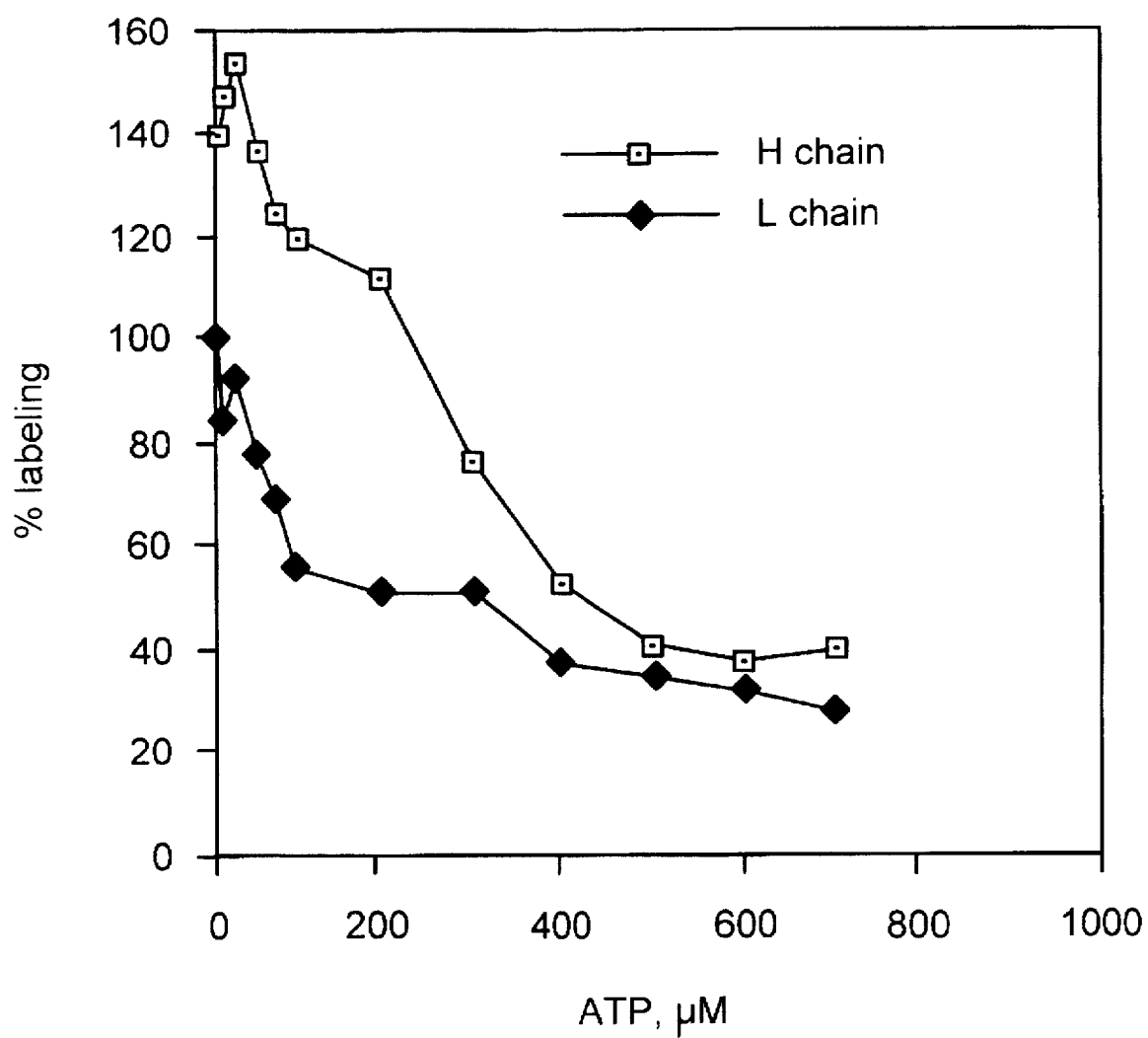

A variety of different monoclonal antibodies, affinity isolated polyclonal antibodies and $F(ab)_2$ fragments from different species were photolabeled with $[\gamma^{32}P]8-N_3ATP$ and analyzed by SDS-PAGE and autoradiography. In FIG. 8 the autoradiograph of photolabeled antibodies shows labeled light and heavy chains with variable degree of incorporation of the photolabel. Minor labeled bands represent degraded antibody fragments. Photolabeling of two of S1C5 and 8019 antibodies with increasing concentrations of $[\gamma^{32}P]8-N_3ATP$ showed saturation effects indicating that limited specific sites are being photomodified (FIGS. 9a and 9b). For S1C5 saturation of photolabeling was observed at approximately 150–175 μM with an apparent $K_d$ of 75 μM. For 8019 saturation was about 50 μM with an apparent $K_d$ of 25 μM, showing that these antibodies have affinity for $8-N_3ATP$. Both light and heavy chains were photolabeled, indicating that the binding site is formed by both chains. Photolabeling could be prevented using ATP for both the antibodies (FIGS. 9c and 9d).

Figure 10A:
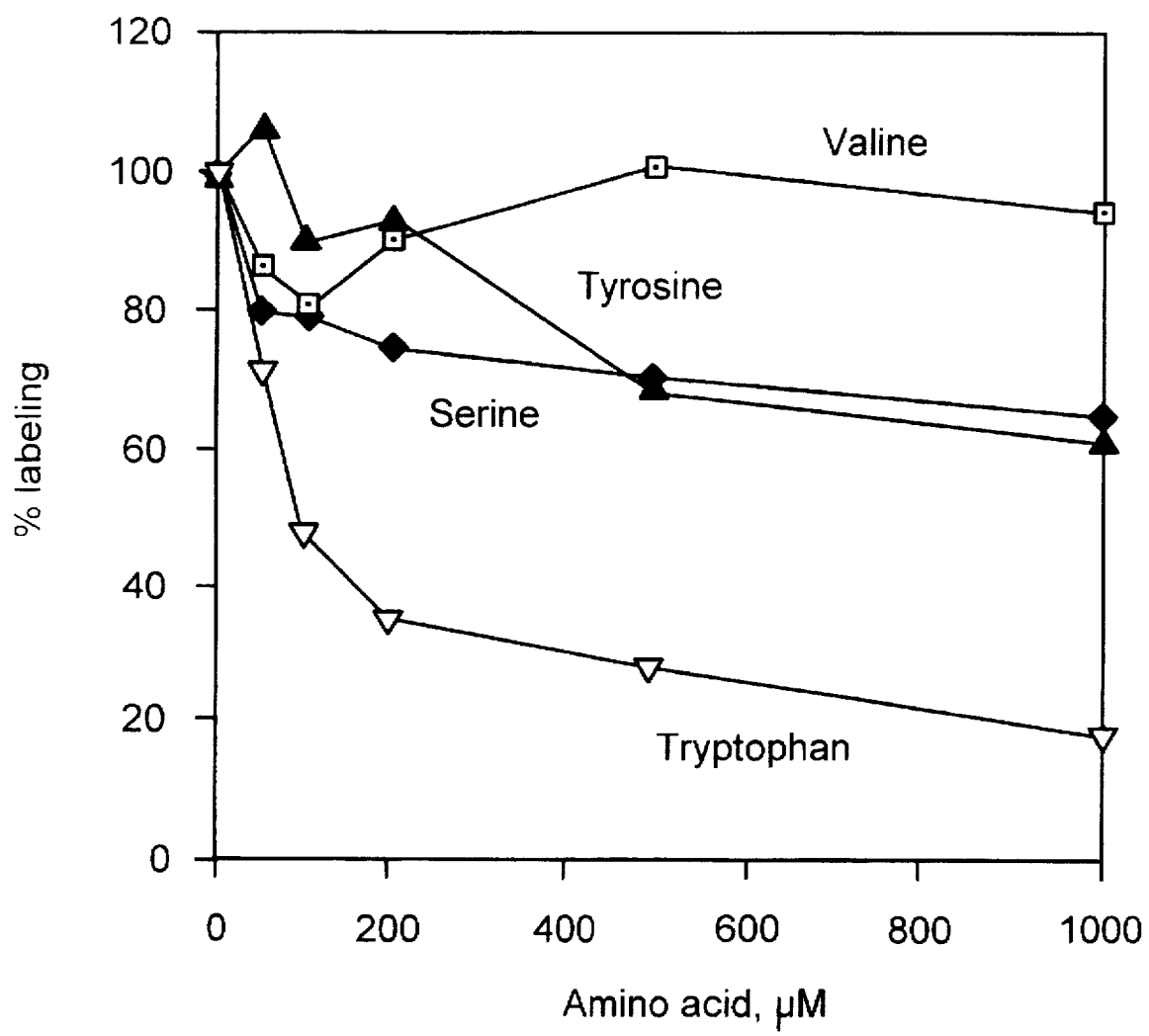
FIGS. 10a and 10b show the results of protection experiments using a variety of amino acids during photoaffinity labeling. The results show that tryptophan provides the best protection indicating that the subject photoaffinity site has affinity for heterocyclic ring structures.
Figure 10B:
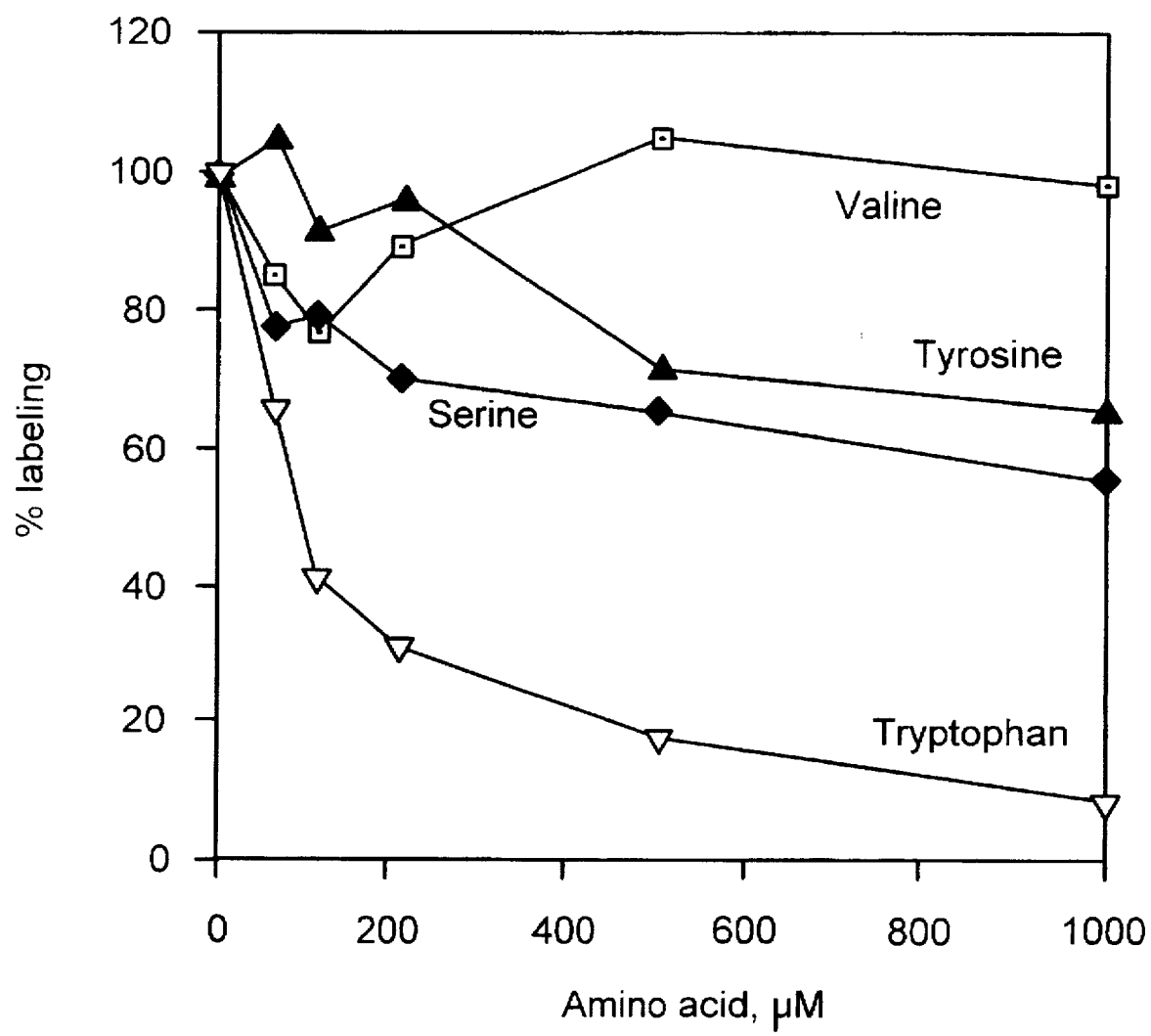

To analyze the specificity of the site for nucleotides, protection experiments were conducted with a variety of nucleotides and nucleosides. Although ATP was able to prevent photolabeling (FIGS. 9c and 9d), other nucleotides (1 mM) afforded about 50–60% protection against photolabeling with 200 μM $[\gamma^{32}P]8-N_3ATP$. Additionally, 8-azidoadenosine proved to have tighter binding than $8-N_3ATP$ (data not shown). Protection experiments using a variety of amino acids, showed that tryptophan produced the best protection (FIGS. 10a and 10b). These experiments demonstrate that this site has affinity for naturally occurring heterocyclic ring structures and suggest that the site is not a typical ATP binding site.

EXAMPLE 11

Antigen Binding of Photo-affinity Labeled Antibodies

Figure 11A:
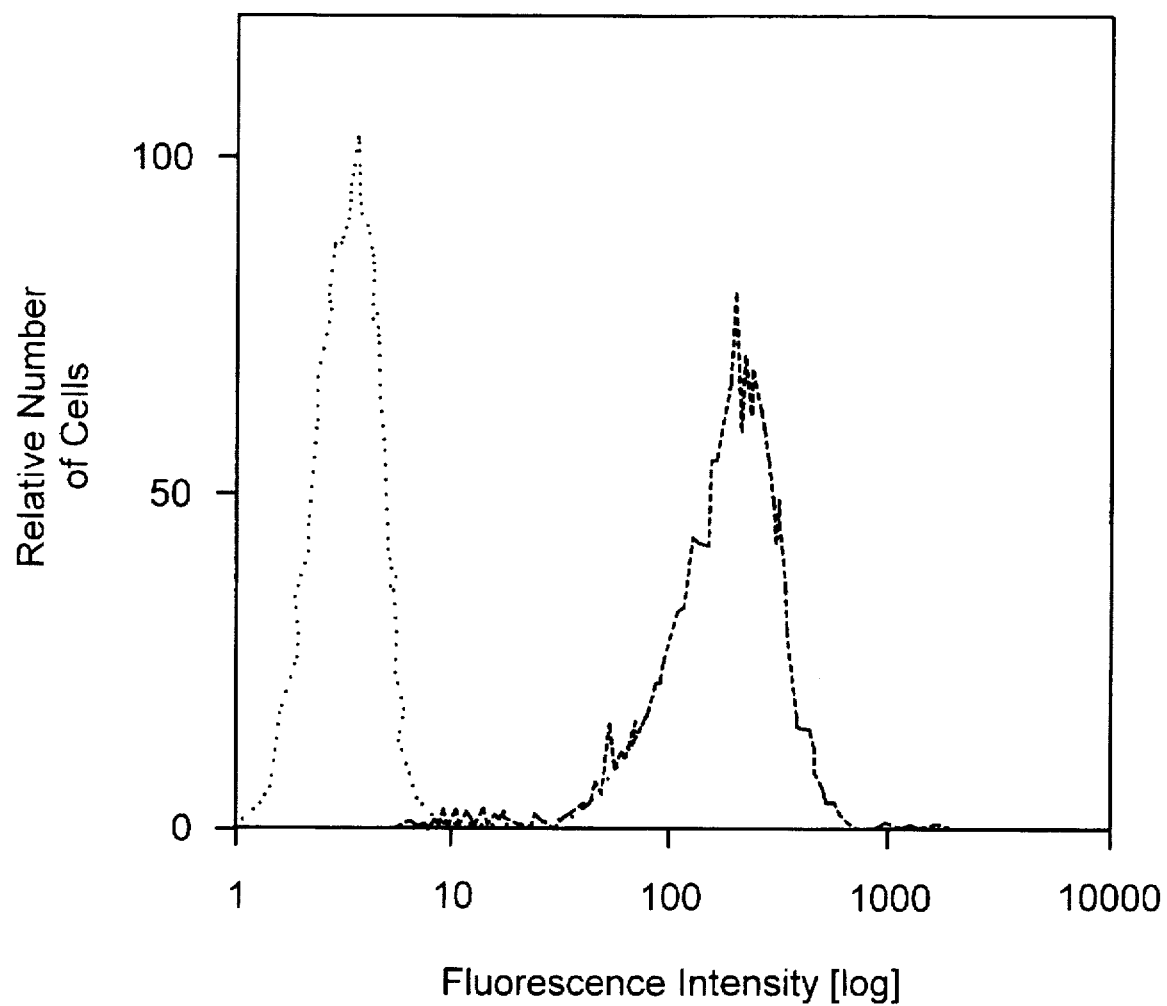
FIGS. 11a and 11b show the results of flow cytometry experiments which show that biotinylated antibodies produced according to the subject photoaffinity attachment procedure bind antigen on specific tumor cell targets.
Figure 11B:
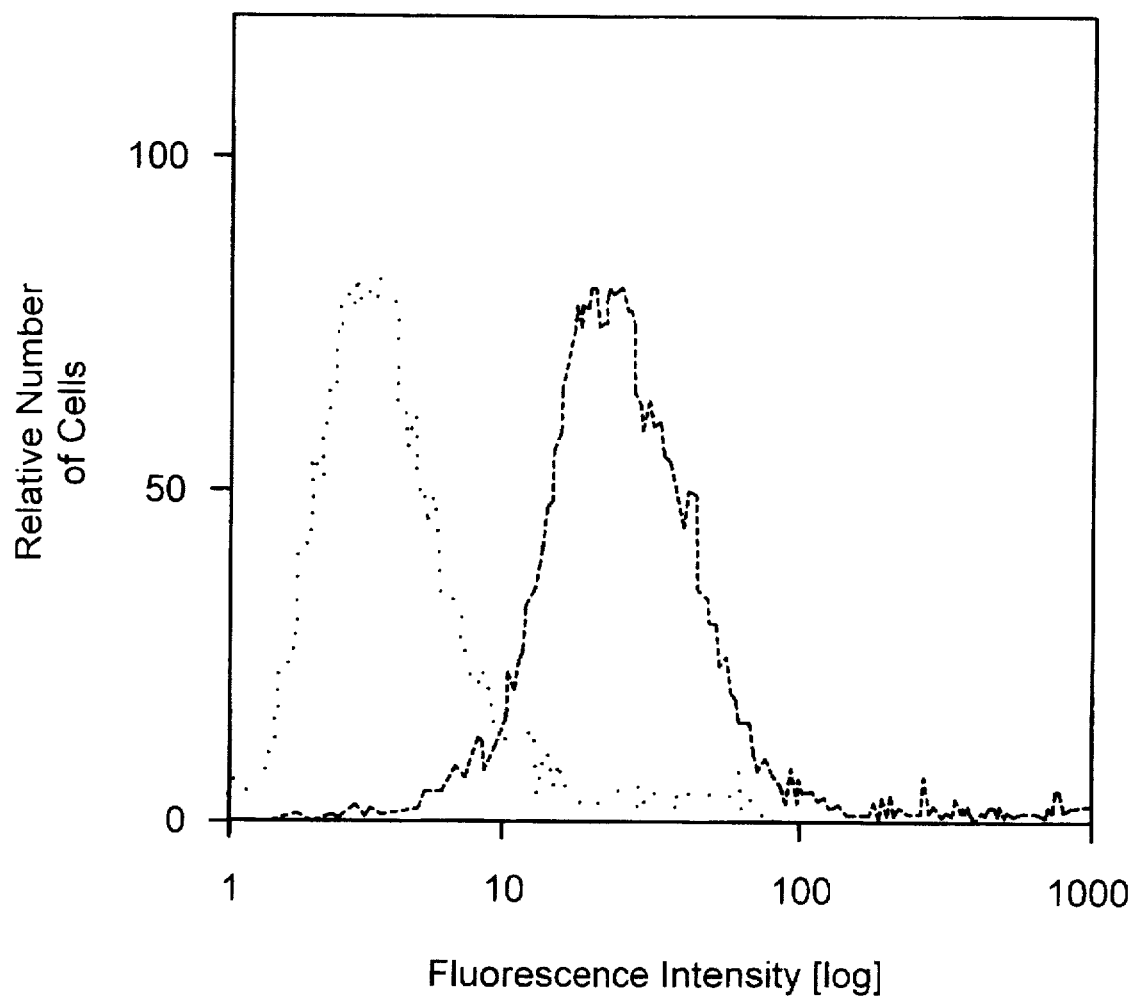

To determine whether the modification of this site affects antigen recognition the binding of photolabeled S1C5 (IgG2a, κ) and 8019 (IgG1, κ) to their respective antigens was tested. S1C5 is specific for a murine B-cell tumor idiotype 38C13 (13) and 8019 recognizes the CEA antigen (Koprowsky et al, *Somat. Cell. Genet.*, 5:957–961 (1979)), expressed by the LS17T4 tumor cell line. The binding of $\gamma^{32}P$-labeled antibody to their cellular targets was inhibited on an apparent 1:1 ratio by unlabeled antibodies (data not shown) indicating that the integrity of the antibody is not disrupted. Also, these same antibodies were photomodified with biotinylated $8-N_3$adenosine and used in FACS. Both biotinylated antibodies recognized their specific tumor cell targets as assayed by flow cytometry (FIGS. 11a and 11b), while biotinylated control antibodies showed no binding indicating that Fc receptors were not involved. A comparison of the photoaffinity biotinylated antibodies with conventionally biotinylated antibodies in FACS produced nearly identical staining (manuscript submitted). Furthermore, we have affinity-biotinylated human immune sera and performed ELISA and Western blots with preparation stored for three months at 4° without detectable loss of reactivity, indicating that the biotin linkage is stable in serum.

EXAMPLE 12

Sequence Alignment of Labeled Peptides

Figure 12A:
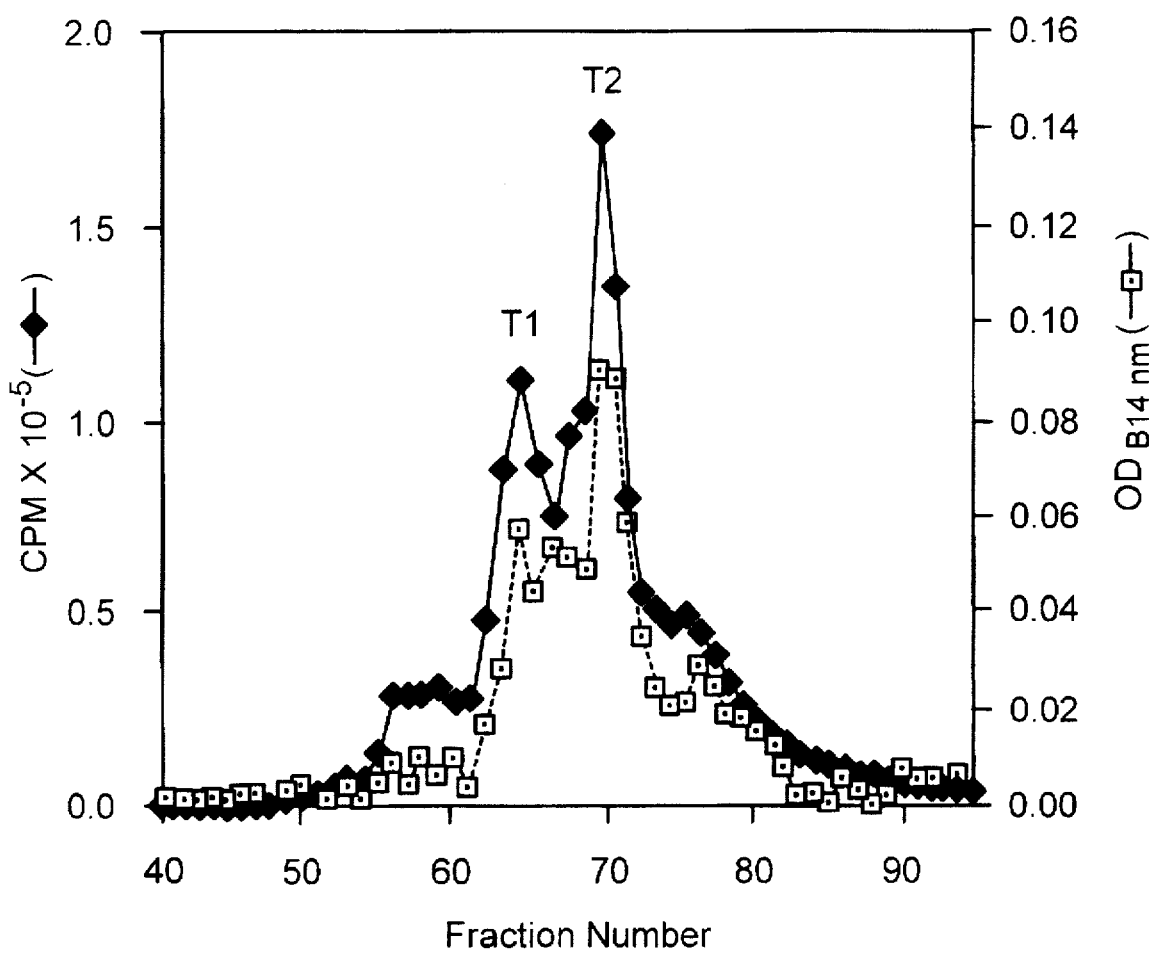
FIGS. 12a and 12b show the results of HPLC purification of tryptic peptides obtained by digestion of photolabeled antibodies produced according to the invention.
Figure 12B:
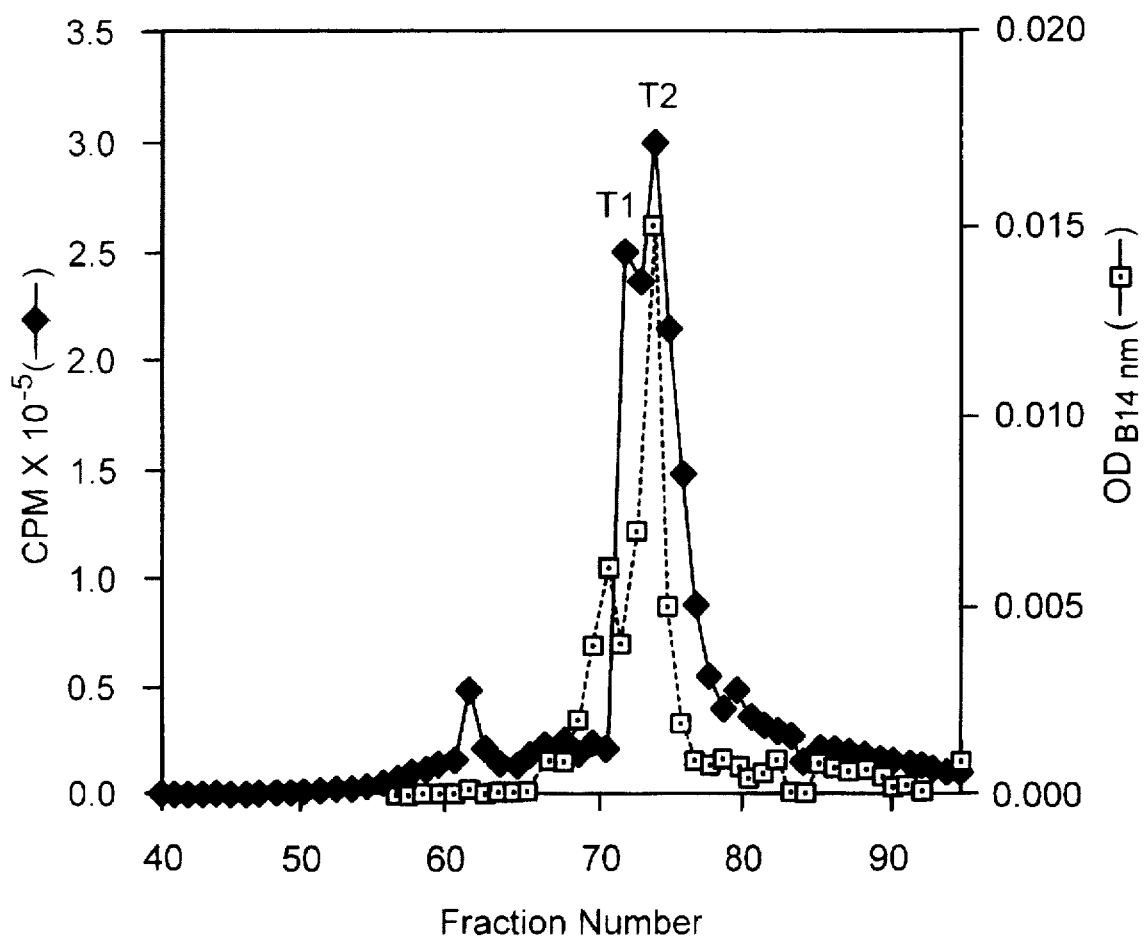

To identify the peptide sequences involved in the formation of the site, each of the antibodies, S1C5 and 8019 were photolabeled with $[\gamma^{32}P]8-N_3ATP$ and digested with trypsin. The tryptic peptides from the photolabeled antibody were purified by a combination of $Al^{3+}$-chelate affinity chromatography and reversed phase HPLC (Shoemaker et al, *Biochemistry*, 32:1883–1890 (1993)). HPLC purification yielded two radioactive peaks with associated UV peaks at 214 nm (FIGS. 12a and 12b). Fractions 64–65 for S1C5 and fraction 71 for 8019 corresponding to the first peak and fractions 70–71 for S1C5 and 73 for 8019 corresponding to the second peak were sequenced.

Amino acid sequence of S1C5 and 8019 were deduced from the cloned and sequenced V genes (FIG. 12c). The identified peptides from photoaffinity labeling corresponded to sequences located in the variable Ig domain. The peptides eluted first (T1) from each antibody are derived from the CDR1 domain of the variable light chain extending into FR2. The second eluted peptides (T2) are from the CDR3-FR4 region of the variable heavy chain domain. It is striking that both peptides included invariant aromatic residues, Trp H103 in the $V_H$ domain and the highly conserved Tyr L36 within the $V_L$ domain. Triplicate experiments using quantitative immuno-precipitation (Harlow et al, *Antibodies, A Laboratory Manual*, Cold Spring Harbor Laboratory, 423–468 (1988)), with [$\gamma^{32}$P]8-N$_3$ATP labeled S1C5 showed an average number of 1.9±0.2 molecules of 8-N$_3$ATP/Ig molecule which is consistent with one [$\gamma^{32}$P]8-N$_3$ATP incorporated into each Fab arm. The isolation of only two photoaffinity labeled peptides per Ig molecule together with the results of the saturation experiments suggested that insertion of photoprobe was directed into a single affinity site which is formed through the participation of both heavy and light chains within the variable domains of immunoglobulins.

EXAMPLE 13

Computer Modeling of ATP Site

The photo-reactive site in tobacco Rubisco activase (Salvucci et al, *Biochemistry*, 33:14879–14886 (1994)), involving base-stacking interactions with tryptophans, has provided the concept for constructing a computer modeled insertion of nucleotide into a known Ig fragment structure. The isolated photo-labeled peptides from both Ig heavy chains contain the invariant Trp residue at position H103, which has the potential of base-stacking with purine rings.

Figure 13A:
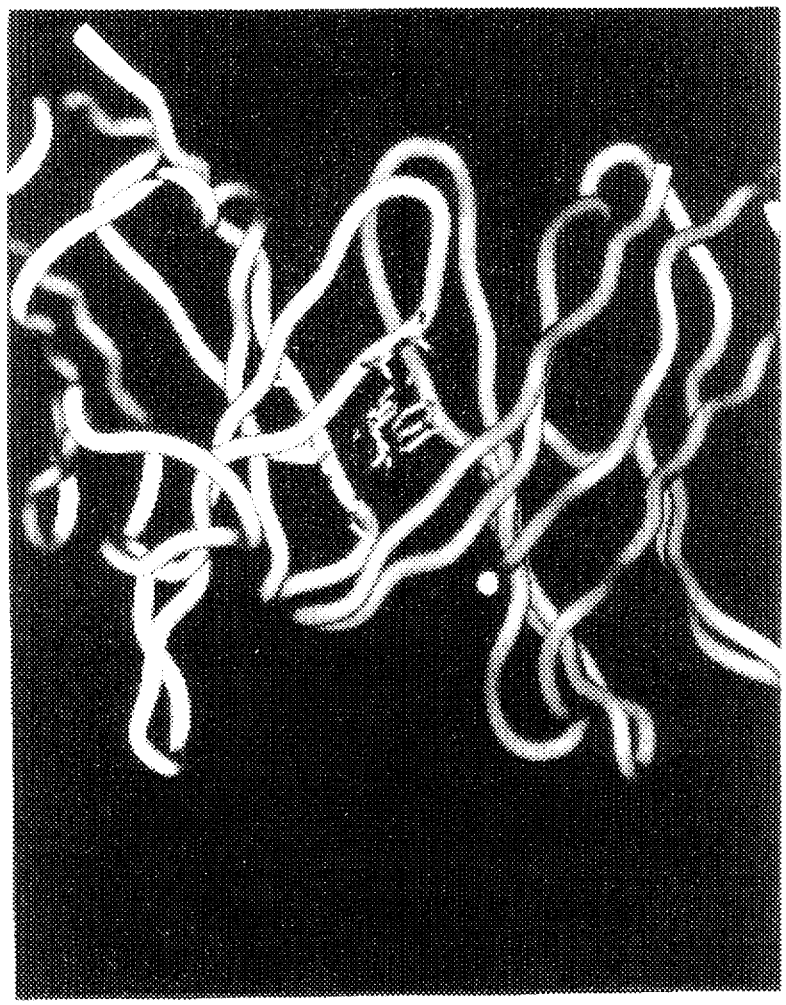
FIGS. 13a and 13b show the overall structure and the location of a nucleotide attached to an antibody according to the invention in relation to the antigen binding site.
Figure 13:
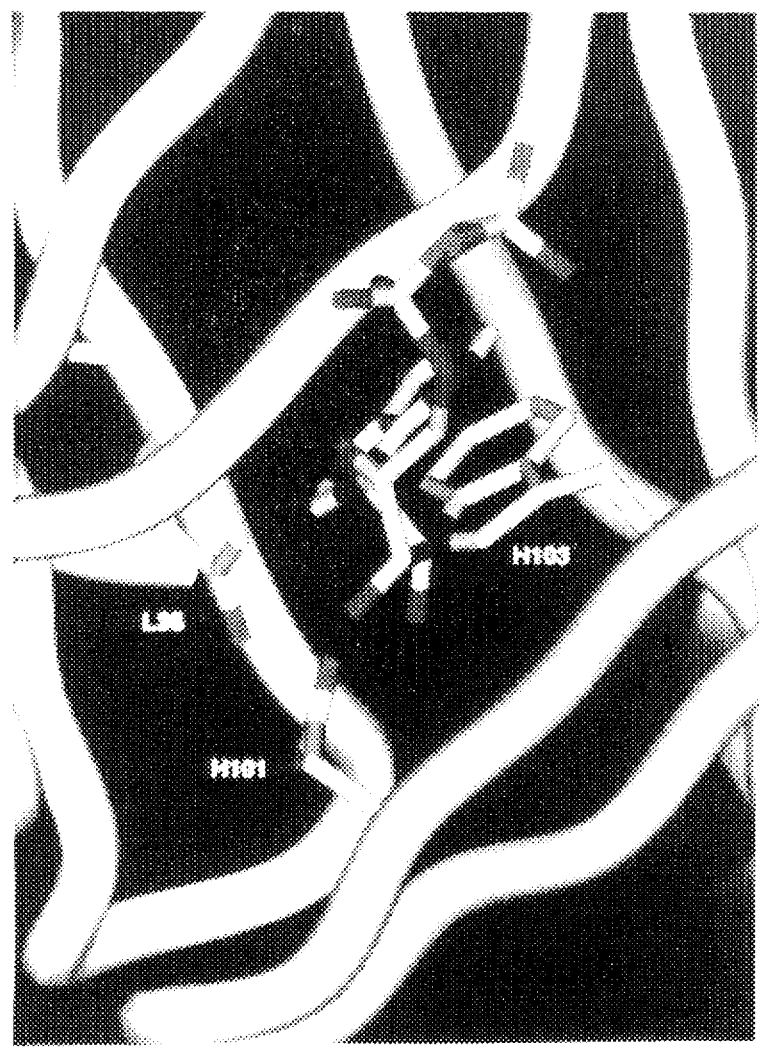

The coordinates of Jel103 Fab were used to model the Fv fragment (Pokkuluri et al, *J. Mol. Biol.*, 243:283–297 (1994)). FIG. 13*a* shows the overall structure and the location of the nucleotide in relation to the antigen binding site. The phosphate groups are exposed to the solvent between the V$_L$ and V$_H$ domains and are visible in the model. In FIG. 13*b*, the predicted contacts of the purine ring with residues H101, H103 and L36 are indicated. The adenosine base is sandwiched between the rings of Trp H103 and Pro L44 providing non-specific stacking interactions. The stacking of the adenosine with the invariant Trp at H103 and the mostly invariant Pro L44 allows sufficient flexibility to label residues from both chains. The azido group at C-8 of the purine ring is in proximity to the hydroxyl of Tyr L36 so that it can form a covalent link upon photolysis. The azido group is also in a position to photoinsert into residues of the CDR3 of heavy chain such as Asp H101 in S1C5 or Glu H100 of 8019. The model exemplifies how the 8-N$_3$ATP probe binds into a hydrophobic pocket at the bottom of the antigen binding site. Since the actual chemical bonds of the reactive nitrene are formed with residues from the hypervariable regions, the CDR3 of the heavy chain and with the conserved Tyr L36 and/or a residue from CDR1 of the light chain, each antibody is expected to be labeled at different residues within the site and with different efficiencies. Photolabeling studies using several antibodies, did show differential labeling of the heavy and light chains (FIG. 8). Although this site has only been identified in two antibodies, most antibodies should possess this site because it involves invariant or conserved residues. This is supported by the fact that all antibodies tested, so far, have been effectively photolabeled.

CONCLUSIONS

These examples provide evidence that antibodies can be modified with a photo-reactive derivative of a biological molecule, e.g., ATP. The labeling kinetics indicate the presence of an unique affinity site for ATP with a kd of 25–75 mmole. The site appears not to be a typical ATP binding site since other nucleotides and aromatic amino acids are potent inhibitors of the photoinsertion. The presence of the affinity site was confirmed by the isolation of labeled peptides from a digestion of two complete antibodies. Interestingly, these peptides are derived from the Fv domains of heavy and light chains, and furthermore, from the same regions in the chains of both antibodies, thereby representing homologous peptides. The peptides from the light chains extend from FR1 over CDR1 to FR2 and the peptides from the heavy chain from FR3 over CDR3 into FR4. Because of the variability in this region the presence of trypsin cleavage sites differs and therefor the length of the peptides is also different. However, the peptides include conserved framework structures, the tryptophan in position 103 of the heavy chain and a less conserved tyrosine in position 37 of the light chain.

Computer modeling of the ATP insertion into an Fv structure shows the close contact to these conserved residues with the probe, in particular a base stacking of the tryptophan with the purine ring of ATP. This model demonstrates several important features which help to understand the interaction of the antibody site with the affinity probe. 1) The site is distant from the CDR loops which make contact with antigen; this explains why photolabeled antibodies still bind antigen. 2) The purine ring penetrates the deepest into the site, while the ribose and the triphosphate are extruding from the molecule and are easily accessible from the molecule surface; this is in full agreement with the ability of the inserted adenosine or ATP probes to carry molecular substitutions with full accessibly, such as the biotin moiety, which can bind avidine. 3) The penetrating purine structure engages in close contacts with conserved heterocyclic amino acid side chains, thereby predicting that most, if not all antibodies carry this site.

ATP is a molecule of great biological importance. These results suggest that nucleotides may play a role in antibody functions. Possible functions involving energy driven mechanisms are the surface movements of the B-cell receptor after cross-linking, the signal transduction of the B-cell receptor, or the folding of Ig chains and release from BiP during synthesis (Haas et al, *Nature*, 306:387–389 (1983)). Recently we discovered an effect of photo-affinity modification on the catalytic activity of light chain dimers (Paul et al, *J. Biol. Chem.*, 270:15257–15261 (1995)). Preliminary studies on photomodified catalytic light chain dimers (unpublished data) showed altered enzyme activity. This indicates that the catalytic site may be influenced by ligands for the novel site described here. Furthermore, the binding to the site by a ligand may have long-range effects over the entire Ig molecule modifying Fc mediated functions like complement fixation and ADDC. These and other Ig effector mechanisms should be examined with respect to changes in activity by ligand binding to the nucleotide affinity site.

Therefore, these results provide further evidence that the subject photoaffinity site comprised in antibodies discovered herein may be exploited for the attachment of diagnostically or medically relevant molecules to antibodies. Antibodies are considered to be ideal vehicles for the delivery of biologically active and medically relevant molecules to selected targets such as tumor cells. However, to date, their practical usefulness in clinical settings has previously been limited because of: (i) incomplete tumor penetration, (ii) immune response against xenogeneic immunoglobulins and (iii) biochemical and structural alteration caused by chemical coupling. Recently significant progress has been made to generate recombinant smaller antibody fragments with improved tissue penetration and favorable pharmacological behavior, also humanized or de novo human antibodies have been produced which do not induce xenograft immune responses in patients. Finally, gene fusion techniques and expression systems have allowed the production of recombinant fusion proteins with improved pharmacokinetics and biodistribution. The subject invention should further improve conventional antibody conjugates because it provides a novel chemical conjugation method which does not affect the structural and biological integrity of the Ig molecule. Moreover, the subject invention is further advantageous in that conjugation occurs at a novel photoaffinity site that is apparently substantially conserved across antibodies of different species and isotype. Therefore, the present invention should have practical advantages over more involved molecular engineering techniques.

In particular, a novel conserved site which is in the Fv domains of the Ig molecule and having affinity for ATP can be used to attach reporter molecules to antibodies without impairing antigen binding, demonstrating the general utility for using the subject affinity photolinker chemistry to attach drugs, metal chelates, antisense oligonucleotides or biologically active peptides to selected antibodies for target-specific delivery.

While the invention has been described in the terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. In a method for immunodetection of an antigen which method detects antigen by a specific antigen-antibody binding reaction wherein the improvement comprises using as the labeled antibody a labeled nucleotide photoaffinity compound-antibody conjugate.

2. The method of claim 1, wherein the immunodetection method is selected from the group consisting of enzyme linked immunosorbent assay (ELISA), radioimmunoassay (RIA), immunoradiometric assay, fluoroimmunoassay, chemiluminescent assay, bioluminescent assay and Western blot.

3. The method of claim 1, wherein the labeled nucleotide photoaffinity compound comprises an ATP- or GTP-analog.

4. The method of claim 3, wherein the labeled nucleotide photoaffinity compound comprises 2-azido-ATP, 8-azido-ATP or benzoylphenone-ATP.

5. The method of claim 1, wherein the label is selected from the group consisting of radiolabels, chromophores, fluorochromes, polyiiucleotides, and enzymes.

6. The method of claim 5, wherein the label is a radiolabel.

7. The method of claim 6, wherein said radiolabeled compound is selected from the group consisting of [$^{32}$P]8N$_3$ATP, [$^{32}$P]2N$_3$ATP and [$^{32}$P]2N$_3$ATP.

8. An immunoconjugate which comprises an antibody conjugated or complexed to one or more moieties having cytotoxic or therapeutic activity wherein the improvement comprises the site-specific attachment of said cytotoxic or therapeutic moieties to a nucleotide photoaffinity compound which has been site-specifically inserted at one or more nucleotide binding sites in the antibody.

9. The immunoconjugate of claim 8, wherein the nucleotide photoaffinity compound is on ATP- or GTP analog.

10. The immunoconjugate of claim 9, wherein said nucleotide binding site has high affinity for purine, azidopurine or heterocyclic bases having a similar structure.

11. The immunoconjugate of claim 9, wherein said ATP- or GTP analog is selected from the group consisting of 2-azido-ATP, 8-azido-ATP and benzoylphenone-ATP.

12. The immunoconjugate of claim 9, wherein the cytotoxic or therapeutic moiety is selected from the group consisting of radiolabels, enzymes, DNA, RNA, toxins, cytokines growth factor, and chelating agents.

13. The immunoconjugate of claim 12, wherein the chelating agent is a triphosphate chelating heavy metal.

14. The immunoconjugate of claim 13, wherein the chelating heavy metal is $^{111}In^{3+}$.

15. The method of claim 1, wherein the label is biotin.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 231 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Gln Ile Val Leu Thr Gln Ser Pro Ala Ile Asn Ser Ala Ser Leu Gly
  1               5                  10                  15

Glu Arg Val Thr Met Thr Cys Thr Ala Ser Ser Ser Val Ser Ser Ser
             20                  25                  30

Tyr Phe His Trp Tyr Gln Gln Lys Gln Gly Ser Ser Pro Lys Leu Trp
         35                  40                  45

Ile Tyr Thr Thr Ser Asn Leu Ala Ser Gly Val Pro Ala Arg Phe Ser
     50                  55                  60

Gly Ser Gly Ser Gly Thr Ser Tyr Ser Leu Thr Ile Ser Ser Met Glu
 65                  70                  75                  80

Ala Glu Asp Ala Ala Thr Tyr Tyr Cys His Gln Tyr His Arg Ser Pro
                 85                  90                  95

Leu Thr Phe Gly Ala Gly Thr Lys Leu Glu Leu Lys Arg Ala Gln Val
             100                 105                 110

Gln Leu Gln Gln Ser Asp Ala Ile Leu Val Lys Pro Gly Ala Ser Val
         115                 120                 125

Lys Ile Ser Cys Lys Ala Ser Gly Tyr Thr Phe Thr Asp His Val Ile
     130                 135                 140

His Trp Val Lys Gln Arg Pro Glu Gln Leu Gly Glu Trp Ile Gly Phe
145                 150                 155                 160

Ile Ser Pro Gly Asn Gly Asp Ile Arg Tyr Asn Glu Lys Phe Lys Asp
                 165                 170                 175

Lys Ala Thr Ala Asp Lys Ser Ser Ser Thr Ala Tyr Met Gln Leu Asn
             180                 185                 190

Ser Leu Thr Ser Glu Asp Ser Ala Val Tyr Phe Cys Lys Arg Ser Phe
         195                 200                 205

Tyr Tyr Tyr Asp Asp Asn Tyr Gly Asp Tyr Trp Gly Gln Gly Thr Thr
     210                 215                 220
```

```
Leu  Thr  Val  Ser  Ser  Ala  Lys
225                 230
```

( 2 ) INFORMATION FOR SEQ ID NO:2:

( i ) SEQUENCE CHARACTERISTICS:
       ( A ) LENGTH: 227 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO:2:

```
Asp  Ile  Val  Leu  Thr  Gln  Ser  Pro  Ala  Ser  Leu  Ser  Ala  Ser  Val  Gly
1              5                        10                       15

Glu  Thr  Val  Thr  Ile  Thr  Cys  Arg  Ala  Ser  Glu  Asn  Ile  Tyr  Ser  Tyr
               20                       25                  30

Leu  Leu  Trp  Tyr  Gln  Gln  Lys  Gln  Gly  Lys  Ser  Pro  Gln  Leu  Leu  Val
          35                      40                       45

Tyr  Asn  Ala  Lys  Thr  Leu  Ala  Glu  Gly  Val  Pro  Ser  Arg  Phe  Ser  Gly
     50                  55                       60

Ser  Gly  Ser  Gly  Thr  Gln  Phe  Ser  Leu  Lys  Ile  Asn  Ser  Leu  Gln  Pro
65                       70                  75                           80

Glu  Asp  Phe  Gly  Ser  Tyr  Phe  Cys  Gln  His  His  Phe  Gly  Thr  Pro  Trp
                    85                  90                                95

Thr  Phe  Gly  Gly  Gly  Thr  Ser  Leu  Glu  Ile  Lys  Arg  Ala  Glu  Val  Asn
               100                      105                 110

Leu  Glu  Glu  Ser  Gly  Gly  Gly  Leu  Val  Gln  Pro  Gly  Gly  Ser  Met  Lys
          115                      120                 125

Leu  Ser  Cys  Ala  Ala  Ser  Gly  Phe  Thr  Glu  Ser  Asp  Ala  Trp  Met  Asp
     130                      135                      140

Trp  Val  Arg  Gln  Ser  Pro  Glu  Lys  Gly  Leu  Glu  Trp  Val  Ala  Glu  Ile
145                      150                      155                      160

Arg  Thr  Lys  Val  Asn  Asn  His  Ala  Thr  Tyr  Tyr  Ala  Glu  Ser  Val  Lys
                    165                      170                      175

Gly  Arg  Phe  Thr  Ile  Ser  Arg  Asp  Asp  Ser  Lys  Ser  Asn  Val  Tyr  Leu
               180                      185                      190

Gln  Met  Asn  Ser  Leu  Arg  Val  Glu  Asp  Thr  Gly  Ile  Tyr  Tyr  Cys  Thr
          195                      200                      205

Met  Ala  Tyr  Tyr  Glu  Ala  Tyr  Trp  Gly  Gln  Gly  Thr  Leu  Val  Thr  Ser
     210                      215                      220

Ala  Ala  Lys
225
```